US009656257B2

United States Patent
Saleh et al.

(10) Patent No.: US 9,656,257 B2
(45) Date of Patent: May 23, 2017

(54) METAL OXIDE SUPPORTED PALLADIUM CATALYST FOR HYDROCARBON OXIDATION

(71) Applicant: UMM AL-QURA UNIVERSITY, Makkah (SA)

(72) Inventors: Saleh Abdel-Mgeed Ahmed Saleh, Makkah (SA); Mohamed Mokhtar Mohamed Abdalla, Benha (EG); Khalid Soliman Khalil Khairou, Makkah (SA)

(73) Assignee: Umm Al-Qura University, Makkah (SA)

( * ) Notice: Subject to any disclaimer, the term of this patent is extended or adjusted under 35 U.S.C. 154(b) by 197 days.

(21) Appl. No.: 14/601,931

(22) Filed: Jan. 21, 2015

(65) Prior Publication Data

US 2016/0207028 A1   Jul. 21, 2016

(51) Int. Cl.
*B01J 23/00* (2006.01)
*B01J 35/00* (2006.01)
(Continued)

(52) U.S. Cl.
CPC ....... *B01J 35/0006* (2013.01); *B01J 23/6447* (2013.01); *B01J 35/004* (2013.01); *B01J 37/036* (2013.01); *B01J 37/10* (2013.01); *C07C 45/36* (2013.01); *B01J 35/002* (2013.01); *B01J 35/0013* (2013.01); *B01J 35/023* (2013.01);
(Continued)

(58) Field of Classification Search
CPC .. B01J 35/0006; B01J 37/036; B01J 23/6447; B01J 37/10; B01J 35/004; B01J 37/0201; B01J 35/0013; B01J 37/08; B01J 37/0018; B01J 35/002; B01J 37/16; B01J 35/023;
(Continued)

(56) References Cited

FOREIGN PATENT DOCUMENTS

| CN | 101530797 A | 9/2009 |
| JP | 6-40961 B2 | 6/1994 |
| JP | 2006-317961 | 11/2006 |

OTHER PUBLICATIONS

Sa et al. "Bi modified Pd/SnO2 catalysts for water denitration" Applied Catalysis B: Environmental vol. 73, Issues 1-2, Apr. 24, 2007, pp. 98-105.*

* cited by examiner

*Primary Examiner* — Colleen Dunn
*Assistant Examiner* — Haytham Soliman
(74) *Attorney, Agent, or Firm* — Oblon, McClelland, Maier & Neustadt, L.L.P.

(57) ABSTRACT

A metal oxide supported palladium catalyst comprised of a β-$Bi_2O_3$/$Bi_2Sn_2O_7$ hetero-junction catalyst support and palladium was developed. The catalyst was synthesized using a sol-gel technique as a nanocrystalline structure. In the presence of fluorene, an oxidant and ultraviolet irradiation, the catalyst converts the hydrocarbon to a mixture of fluorenol/fluorenone oxidation products. The close proximity between β-$Bi_2O_3$ and $Bi_2Sn_2O_7$ heterojunction phases in the catalyst is thought to be responsible for the efficient charge separation and catalytic activity. An indirect chemical probe method using active species scavengers elucidated that the photo-oxidation mechanism proceeds via holes and superoxide radical ($O_2.^-$) moieties.

21 Claims, 17 Drawing Sheets

(51) Int. Cl.
*B01J 37/03* (2006.01)
*B01J 37/10* (2006.01)
*B01J 23/644* (2006.01)
*C07C 45/36* (2006.01)
*B01J 35/02* (2006.01)
*B01J 35/10* (2006.01)
*B01J 37/16* (2006.01)
*B01J 37/08* (2006.01)
*B01J 37/00* (2006.01)
*B01J 37/02* (2006.01)

(52) U.S. Cl.
CPC ........ *B01J 35/1009* (2013.01); *B01J 35/1014* (2013.01); *B01J 35/1038* (2013.01); *B01J 35/1061* (2013.01); *B01J 37/0018* (2013.01); *B01J 37/0201* (2013.01); *B01J 37/08* (2013.01); *B01J 37/16* (2013.01)

(58) Field of Classification Search
CPC  B01J 35/1038; B01J 35/1009; B01J 35/1061; C07C 45/36
USPC ........................................................ 502/325
See application file for complete search history.

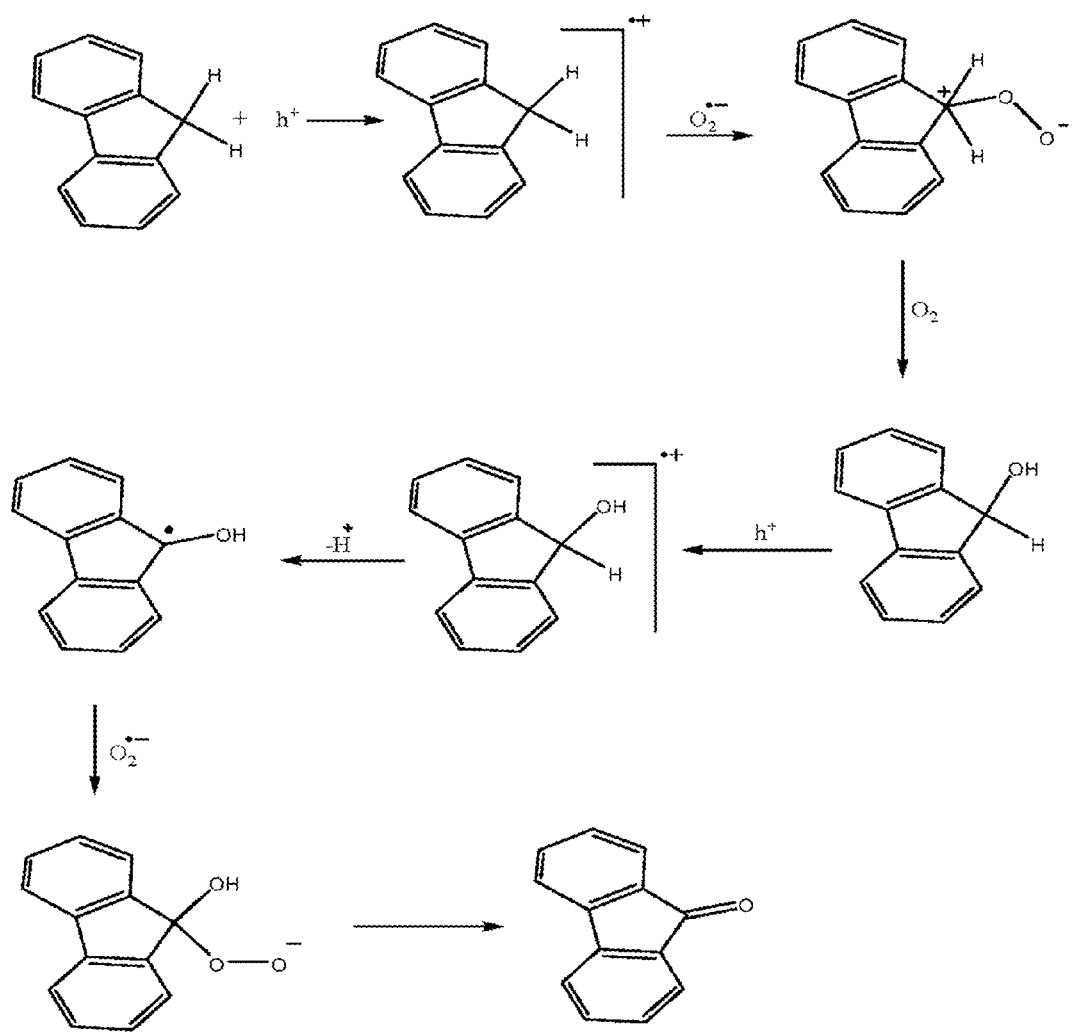
Fig. 11: Proposed Mechanism for the photocatalytic oxidation of fluorene

METAL OXIDE SUPPORTED PALLADIUM CATALYST FOR HYDROCARBON OXIDATION

BACKGROUND OF THE INVENTION

Technical Field

The present invention relates to a metal oxide supported palladium catalyst, the preparation thereof, and its use for the oxidation of hydrocarbon compounds. More specifically, the present invention relates to a $\beta\text{-}Bi_2O_3/Bi_2Sn_2O_7$ heterojunction supported palladium catalyst for fluorene oxidation under ultraviolet irradiation.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Aromatic hydrocarbons, especially polycyclic aromatic hydrocarbons (PAHs) and other organic compounds found in association with PAHs, are potent carcinogens and teratogens for a variety of organisms. Many of these chemicals are implicated in serious human disease states such as respiratory diseases and cancer [D. B. Kittelson, J. Aerosol Sci. 29 (1998) 575-588—incorporated herein by reference in its entirety]. PAHs currently represent the most abundant man-made pollutant on earth. These chemicals possess relatively long residence times and can enter into the atmosphere, rivers and soil through a variety of means including evaporation, diffusion and permeation. Fluorene, one such polycyclic aromatic hydrocarbon (PAH), is formed during the combustion of fossil fuels, incomplete fuel combustion [O. Gimeno, F. J. Rivas, F. J. Beltran, M. Carbajo, Chemosphere 69 (2007) 595-604—incorporated herein by reference in its entirety], asphalt production [J. P. Buchet, J. P. Gennart, F. Mercado-Calderon, J. P. Delavignette, L. Cupers, R. Lauwerys, Br J Ind Med 49 (1992) 761-768—incorporated herein by reference in its entirety] and automotive exhaust emissions [M. Baerns, H. Borchert, R. Kalthoff, P. KaDner, F. Majunke, S. Trautmann, A. Zein, P. Ruiz and B. Delmon (Eds.) Catalysis *Studies in Surface Science and Catalysis*, Vol. 12, pp. 51-60; J. Bünger, J. Krahl, A. Weigel, O. Schröder, T. Brüning, M. Müller, E. Hallier, G. Wesphal, Arch. Toxicol. 80 (2006) 540-546; J. Sabate, J. M. Bayona, A. M. Solanas, Chemosphere 44 (2001) 119-124—each incorporated herein by reference in its entirety]. Like many PAHs, fluorene is reported to possess potent mutagenic and carcinogenic properties [H. T. Yu, J Environ Sci. Health Part C: Environ Carcinog & Ecotoxicol Rev. 20 (2002) 149-83; Y. C. Lin, W. J. Lee, H. C. Hou, Atmos. Environ. 40 (2006) 3930-3940—each incorporated herein by reference in its entirety].

Owing to their toxicity, the degradation and removal of PAHs has been the focus of numerous studies [L. Liu, B. Yang, H. Zhang, S. Tang, Z. Xie, H. Wang, Z. Wang, P. Lu, Y. Ma, J. Phys. Chem. C, 112 (2008) 10273-10278—incorporated herein by reference in its entirety]. Photocatalytic oxidation is one strategy used for the degradation of PAHs [M. M. Mohamed, S. A. Ahmed, K. S. Khairou, Appl. Catal. B: Environ. 150-151 (2014) 63-73—incorporated herein by reference in its entirety], which involves the use of visible light irradiation in lieu of high temperatures and/or harsh/toxic oxidants that are commonplace in traditional oxidative catalysis [N. T. Vandenborre, E. Husson, H. Brusset, Spectrochim. Acta A 37 (1981) 113—incorporated herein by reference in its entirety]. While complete oxidation without a photocatalyst is thermodynamically possible, this process is kinetically slow and is therefore not ideal. The removal of fluorene, through oxidative degradation pathways to furnish fluorenol/fluorenone products, has only been accomplished on small scale and through the use of harsh oxidants [S. M. Correa, G. Arbilla, Atmos. Environ. 40 (2006) 6821-6826—incorporated herein by reference in its entirety]. A benefit of pursuing such fluorene oxidative removal strategies is that the fluorenone/fluorenol products can be utilized as building blocks for the synthesis of antimalarial drugs, insecticides, algaecides, biopharmaceutical dyes and optical brightening agents [D. Dunn, G. Hostetler, M. Iqbal, V. R. Marcy, Y. G. Lin, B. Jones, L. D. Aimone, J. Gruner, M. A. Ator, E. R. Bacon, S. Chatterjee, Bioorganic & Medicinal Chemistry Letters 22 (11) (2012) 3751-3753—incorporated herein by reference in its entirety]. In addition, their light and temperature sensitivities, heat resistance, conductivity and corrosion resistance make fluorenol/fluorenone useful materials in the areas of thermo and light sensitization, luminescence chemistry, spectrophotometric analysis and molecular chemistry [T. A. M. Ferenczi, M. Sims and D. D. C. Bradley J. Phys.: Condens. Matter 20(4) (2008) 045220-045224; L. Feng, C. Zhang, H. Bie, Z. Chen, Dyes & Pigments 64 (2005) 31-40—incorporated herein by reference in its entirety].

The most common photocatalytic oxidative systems generally include one or more ultraviolet (UV) energy sources for irradiating UV light onto an organic substrate in the presence of a photocatalyst. Titanium dioxide ($TiO_2$) remains the most popular and most prevalent photocatalyst because it is a light, strong, anti-corrosive, and inexpensive material. When excited by radiation with a wavelength less than 400 nm (radiation in the near-UV range), titanium dioxide photocatalysts generate electron/hole pairs ($h^+$), which act as strong oxidizing agents to adsorbed species. In the presence of molecular oxygen and/or water, these electron/hole pairs can lead to superoxide ($O_2-$.) or hydroxyl radicals (OH.), which can then in turn oxidize and degrade organic matter.

Although the use of titanium dioxide as a photocatalyst has been widespread, other photocatalysts have also used been used including: stannic oxide, zinc oxide, vanadium oxide, dibismuth trioxide, tungsten trioxide, ferric oxide, zirconium oxide, antimony oxide, and cerium oxide (K. Garfield, J. Potter, U.S. Pat. No. 7,820,100 B2—incorporated herein by reference in its entirety). As is the case with these materials, many photocatalytic systems involve the use of one metal or metal oxide. The use of multiple metals and/or metal oxides for photocatalytic oxidation is less explored. Bismuth oxide ($Bi_2O_3$) is an attractive material for oxidative photocatalysis because of its good electrical conductivity and thermal properties. It is extensively used in various applications such as microelectronics, sensor technology and optical coatings [W. D. He, W. Qin, X. H. Wu, X. B. Ding, L. Chen, Z. H. Jiang, Thin Solid Films 515 (2007) 5362-5365; S. J. A. Moniz, D. Bhachu, C. S. Blackman, A. J. Cross, S. Elouali, D. Pugh, R. Q. Cabrera, S. Vallejos, Inorg. Chim. Acta 380 (2012) 328-335—each incorporated herein by reference in its entirety]. As a photocatalyst, $Bi_2O_3$ is a p-type semiconductor with conduction and valence band edges +0.33 and +3.13 V relative to Normal hydrogen electrode (NHE), respectively. These values account for its capability to oxidize water and possibly generate highly reactive species, such as $O_2-$. and OH. radicals, which may act as initiators for oxidation reactions.

On the other hand, SnO$_2$ is an important n-type wide-band gap semiconductor with broad applications based on electrical and optical properties of the oxide, which can also be used as strong oxidation catalysts [N. Van Hieu, L. T. B. Thuy, N. D. Chien, Sensors and Actuators B 129 (2008) 888-895—incorporated herein by reference in its entirety].

There is ongoing research to identify new bismuth and tin oxide containing materials with unique properties for various applications, such as photocatalysis. Wang et al. (Chinese Patent No. CN101530797A—incorporated herein by reference in its entirety) disclosed a core-shell structured catalyst comprising a mixture of tin dioxide and bismuth oxide wherein a noble metal such as palladium (Pd) is distributed on the surface of the core material. This mixed oxide core-shell catalyst can be used for carbon monoxide oxidations, methanol and alcohol electro-oxidations, and oxygen electro-reduction chemistry.

Hiroshi et al. (Japanese Patent No. JP6040961B2—incorporated herein by reference in its entirety) disclosed the preparation of an alcohol/aldehyde oxidation catalyst by supporting palladium, bismuth, and tin on an inorganic support.

Kobayashi, H. (Japanese Patent No. JP04348351B2—incorporated herein by reference in its entirety) disclosed a photocatalyst containing palladium along with a mixture of bismuth oxide and tin oxide for use as a decomposition product oxidant.

In view of the forgoing, the objective of the present invention is to synthesize new and active catalysts comprised of multiple metals/metal oxides capable of converting fluorene to fluorenol/fluorenone using a mild oxidant and ultraviolet irradiation.

BRIEF SUMMARY OF THE INVENTION

According to a first aspect, the present invention relates to a metal oxide supported palladium catalyst, where the metal oxide support comprises a bismuth oxide and a bismuth-tin oxide phase, and palladium is embedded within the catalyst support.

In one or more embodiments, the bismuth oxide phase comprises β-Bi$_2$O$_3$ and the bismuth-tin oxide phase comprises Bi$_2$Sn$_2$O$_7$ In one or more embodiments, the β-Bi$_2$O$_3$ and Bi$_2$Sn$_2$O$_7$ are present as a mixture of different crystalline phases and the distance between the β-Bi$_2$O$_3$ and Bi$_2$Sn$_2$O$_7$ lattice fringes is between 1.3 Å and 1.6 Å.

In one embodiment, the atomic ratio of bismuth to tin is 4:1 to 2:1 based on the total number of bismuth and tin atoms in the catalyst support.

In one embodiment, the metal oxide supported palladium catalyst contains 0.1-3.0% palladium by weight based on the total weight of the catalyst support.

In one embodiment, the catalyst is in the form of a crystalline nanoplate-like structure with an average size of 30-60 nm.

In one embodiment, the catalyst is in the form of a crystalline nanoplate-like structure with a specific surface area of 5-25 m$^2$g$^{-1}$.

In one embodiment, the catalyst is in the form of a crystalline nanoplate-like structure with a pore volume of 0.10-0.25 cm$^3$/g-Å.

In one embodiment, the catalyst is mesoporous with pore diameters ranging from 2.0-50.0 nm.

In one embodiment, the catalyst is palladium and is affixed inside the pores of the catalyst support.

According to a second aspect, the present invention relates to a process for producing a metal oxide supported palladium catalyst comprising mixing a first solution comprising bismuth ions and a second solution comprising tin ions in the presence of a polymeric template to form a sol-gel, doping the sol-gel with palladium ions, and reducing the palladium ions.

In one embodiment, the atomic ratio of bismuth ions to tin ions is 4:1 to 2:1 based on the total number of bismuth and tin atoms in the bismuth and tin ion solutions.

In one embodiment, the template is polyethylene glycol.

In one embodiment, the template is polyethylene glycol with a weight average molecular weight range of 1,000-3,000 g/mol.

In one or more embodiments, the process for producing the metal oxide supported palladium catalyst comprises adding an ammonia solution to the bismuth-tin ion solution, heating, autoclaving the formed gel, vacuum drying, and calcining.

In one embodiment, the source of palladium ions is Pd(NO$_3$)$_2$.

In one embodiment, the source of bismuth ions is Bi(NO$_3$)$_3$.5H$_2$O.

In one embodiment, the source of tin ions is Sn(NO$_3$)$_4$.

In one embodiment, the sol-gel was formed by reacting a 1-20% (v/v) ammonia solution with the bismuth and tin ion solutions at 50-100° C.

In one embodiment, the catalyst is calcined at 300-700° C.

According to a third aspect, the present invention relates to a method of reacting an oxidant and a hydrocarbon under ultraviolet irradiation in the presence of the metal oxide supported palladium catalyst.

In one embodiment, the hydrocarbon is a polycyclic aromatic hydrocarbon.

In one embodiment, the hydrocarbon is fluorene, and the reacting forms a mixture comprising fluorenol/fluorenone oxidation products In one embodiment, the hydrocarbon is fluorene, and the reacting forms oxidative degradation byproducts, such as dibenzofuran and phthalic anhydride, in less than 1% yield.

In one embodiment, the oxidant is molecular oxygen, and is passed through the reaction mixture for 1-60 minutes at a rate of 1-60 ml/min.

In one or more embodiments, the ultraviolet irradiation source is a high pressure mercury lamp (125 W) with an average light intensity of 50-70 mWcm$^{-2}$ producing ultraviolet light with a wavelength in between 320 and 400 nm.

In one or more embodiments, the metal oxide supported palladium catalyst and fluorene are dispersed in a solvent, purged with molecular oxygen, and irradiated.

In one embodiment, the catalyst loading is 100-300 mg per 350 ml of fluorene.

In one embodiment, the reaction medium is a polar aprotic solvent, such as acetonitrile.

In one embodiment, the metal oxide supported palladium catalyst is recovered and reused in 1-10 reaction iterations.

In one embodiment, an active species scavenger, such as isopropanol, p-benzoquinone, and triethanolamine, is added to attenuate the reactivity of the metal oxide supported palladium catalyst.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 11 is a scheme illustrating the proposed mechanism for the photocatalytic oxidation of fluorene to fluorenol/fluorenone.

DETAILED DESCRIPTION OF THE EMBODIMENTS

Figure 1:
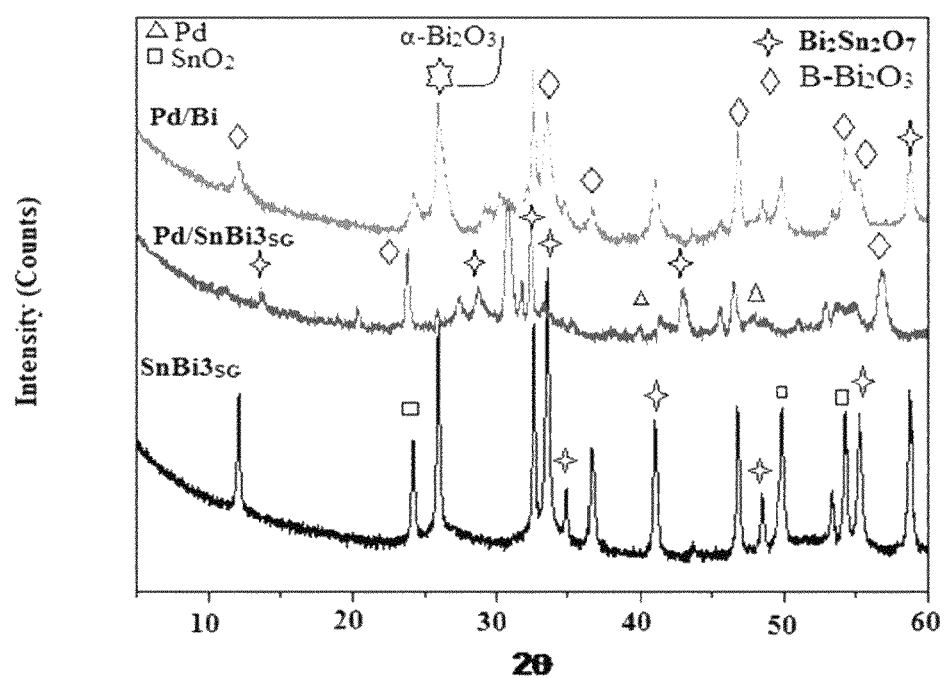
FIG. 1 is a graph illustrating the XRD patterns of $SnBi3_{SG}$, $Pd/Bi_{SG}$ and $Pd/SnBi3_{SG}$ obtained at room temperature.

Referring now to the drawings, wherein like reference numerals designate identical or corresponding parts throughout the several views.

The present invention pertains to a mixed metal oxide supported palladium catalyst, where the metal oxide support comprises a bismuth oxide and a bismuth-tin oxide phase and palladium is embedded within the catalyst support. Furthermore, the present invention relates to the preparation of the metal oxide supported catalyst, and its use for the oxidation of hydrocarbon compounds under ultraviolet irradiation.

As used herein, a catalyst is a substance that can cause a change in the rate of a chemical reaction without itself being consumed in the reaction. Catalysts are generally characterized as either heterogeneous or homogeneous. Heterogeneous catalysts exist in a different phase than the reactants (e.g. a solid metal catalyst and liquid phase reactants), and the catalytic reaction generally occurs on the surface of the heterogeneous catalyst. Thus, for the catalytic reaction to occur, the reactants must diffuse to and/or adsorb onto the catalyst surface. This transport and adsorption of reactants is often the rate limiting step in a heterogeneous catalysis reaction. Heterogeneous catalysts are also generally easily separable from the reaction mixture by common techniques such as filtration or distillation, and can sometimes be re-used in subsequent catalytic processes.

As used herein, photocatalysis is the acceleration of a photoreaction in the presence of a catalyst. In photogenerated catalysis, the photocatalytic activity depends on the ability of the catalyst to generate electron-hole pairs, which in turn generate free radicals (e.g. hydroxyl radicals: .OH) able to undergo secondary reactions.

In accordance with the present invention there is provided a catalyst which comprises a support having a plurality of metal particulates. The metal particulates may be affixed to the support in any reasonable manner, such as affixed to the surface of the support or alternately, at least partially embedded within the support or both. Preferably, the particles are embedded within the support. When used herein to refer to additional catalytic elements and a metal oxide, the term embedded means that the additional elements are integral to, or highly connected and incorporated with, the metal oxide, as opposed to being present only on the surface of the metal oxide or in physical blends of preformed material. Moreover, the metal particulates can be embedded within the metal oxide in a number of ways, which include but are not limited to being sandwiched between two metal oxide phases, encapsulated within a support cavity, or embedded within pores found in the metal oxide support. In a preferred embodiment, the metal particulates are affixed inside the pores of the catalyst support. Furthermore, without additional qualifiers, mesoporous refers to a material that includes pores with diameters in a range from about 2.0 to 50.0 nm. In one embodiment, the catalyst affixed within the metal oxide is palladium. In one embodiment, the metal oxide supported palladium catalyst contains 0.1-3.0% palladium by weight based on the total weight of the catalyst support, preferably 1.5-2.5%, more preferably 1.8-2.2%, even more preferably 1.9-2.1%. The catalyst is in the form of a crystalline nanoplate-like structure with an average size of 30-60 nm, preferably 40-50 nm. In another embodiment, the catalyst is in the form of a crystalline nanoplate-like structure with a specific surface area of 5-25 $m^2g^{-1}$, preferably 10-15 $m^2g^{-1}$. The catalyst is in the form of a crystalline nanoplate-like structure with a pore volume of 0.10-0.25 $cm^3/g$-Å, preferably 0.13-0.20 $cm^3/g$-Å, even more preferably 0.15-0.16 $cm^3/g$-Å. The pore size may have a narrow monomodal, bimodal, or multimodal distribution. In one embodiment, the catalyst shows a trimodal distribution with pore diameters ranging from 2.0-50.0 nm, preferably 2.0-25.0 nm, even more preferably 2.1-21.0 nm. The porous materials may also be manufactured via a templating process described hereafter.

For purposes of the present invention the catalyst support refers to a high surface area material to which a catalyst is affixed. The support may be inert or may participate in catalytic reactions. In the present invention, the mixed metal oxide support is composed of bismuth and tin cations in one or more possible oxidation states in combination with oxide anion $O^{-2}$ wherein the metal oxide is represented by any or all of $Bi_xO_z$, $Sn_yO_z$, $Bi_xSn_yO_z$, wherein x, y, z are equal to or greater than 1. In one embodiment, the atomic ratio of bismuth to tin is between 1:1-5:1, preferably 2:1-4:1, more preferably 2.5:1-3.5:1 based on the total number of atoms in the catalyst support.

The catalyst support may be comprised of a plurality of different crystallographic phases. In one embodiment, the bismuth oxide phase comprises at least one of five crystallographic polymorphs: $\alpha$-$Bi_2O_3$, $\beta$-$Bi_2O_3$, $\gamma$-$Bi_2O_3$, $\delta$-$Bi_2O_3$, $\epsilon$-$Bi_2O_3$ phase, preferably a $\beta$-$Bi_2O_3$ phase. For purposes of the present invention, $\beta$-$Bi_2O_3$ refers to a crystallographic polymorph of bismuth oxide that forms a tetragonal structure indicated by $2\theta=31.5°$ and $32.1°$ peaks using XRD analysis. In another embodiment, the bismuth-tin oxide phase comprises a mixture of $SnO_2$, $Bi_2O_3$, and $Bi_2Sn_2O_7$, preferably $Bi_2Sn_2O_7$. For purposes of the present invention, the presence of a $Bi_2Sn_2O_7$ phase is indicated by $2\theta=32.5°$, $35°$ peaks using XRD analysis. In one embodiment, the $\beta$-$Bi_2O_3$ and $Bi_2Sn_2O_7$ are present as a mixture of different crystalline phases within the catalyst support and the distance between the $\beta$-$Bi_2O_3$ and $Bi_2Sn_2O_7$ lattice fringes is between 1.0 Å-2.0 Å, preferably 1.2 Å-1.7 Å, more preferably 1.3 Å-1.6 Å. The crystal lattice refers to an array of points repeating periodically in three dimensions to make up a unit cell, which is represented in terms of its lattice parameters.

The present invention relates to a process for producing a metal oxide supported palladium catalyst using a sol-gel technique. The sol-gel technique is a process for producing solid materials from small molecules, through a process involving conversion of monomers into a colloidal solution (sol) that acts as the precursor for an integrated network (or gel) of either discrete particles or network polymers.

The photocatalyst is prepared by mixing a $1^{st}$ solution comprising bismuth ions and a $2^{nd}$ solution comprising tin ions in the presence of a polyethylene glycol template to form a sol-gel, doping the sol-gel with palladium ions, and reducing the palladium ions. The aqueous solutions may include salts and/or other ingredients.

In terms of the present invention, templating refers to a controlled patterning and template refers to the addition of any material that determines control of an imposed pattern and may include molecular self-assembly. The templating agents may facilitate the production of substrates with directionally aligned tubular meso-channel forms, or pores. Control of the pore characteristic may, in turn, provide control of the particle size of catalytic metal by reducing the catalytic metal ability or propensity to agglomerate. The particle size of catalytic metal may be controlled, with respect to pore formation of the porous template, by controlling or affecting one or more of pore size, pore distribution, pore spacing, or pore dispersity.

Selection of the type(s) and amounts of the templating agent may affect or control the pore characteristics of the resultant templated substrate. In one embodiment, the templating agent may include one or more cyclic or linear polymeric species, such as crown ethers or polyethylene glycol chains.

Crown ethers are heterocyclic chemical compounds that include a ring that includes several ether groups. Suitable crown ethers may include oligomers of ethylene oxide, the repeating unit being ethyleneoxy, i.e., —$CH_2CH_2O$—. Useful members of this series may include the tetramer (n=4), the pentamer (n=5), and the hexamer (n=6). Crown ethers derived from catechol may be used in the templating agent. Crown ethers that strongly bind certain types of cations to form complexes may be included in the templating agents. The oxygen atoms in the crown ether may coordinate with a cation located at the interior of the ring, whereas the exterior of the ring may be hydrophobic.

In certain embodiments of the foregoing method, the linear polymer template may be comprised of PVP (polyvinlpyrrolidone), PVA (polyvinylalcohol), PEI (polyethyleneimine), PEG (polyethyleneglycol), polyethers, polyesters, polyamides, dextran, sugar polymers, functionalized hydrocarbon polymers, functionalized polystyrene, polylactic acid, polycaprolactone, polyglycolic acid, poly(ethylene glycol)-polypropylene glycol)-poly(ethylene glycol) or copolymers or combinations thereof. In one embodiment, the template is polyethylene glycol with a weight average molecular weight range of 300-5,000 g/mol, preferably 1,000-3,000 g/mol, more preferably 1,800-2,200 g/mol. In another embodiment, the template is polyethylene glycol with a weight average molecular weight range of 300-10,000 g/mol, preferably 3,000-7,000 g/mol, more preferably 5,500-6,500 g/mol.

An ion source for palladium, bismuth, and tin ions used in the metal oxide supported palladium photocatalyst according to the invention, suffices to be a water soluble salt, examples of which can be a water soluble salt such as palladium(II) nitrate, palladium(II) sulfate, palladium(II) acetate, tetraamminepalladium(II) nitrate, bismuth(III) sulfate, bismuth(III) nitrate, bismuth(III) chloride, tin(IV) chloride, tin(IV) nitrate and the like, preferably $Pd(NO_3)_2$, $Bi(NO_3)_3$, $Sn(NO_3)_4$, and hydrates thereof.

In one embodiment, the atomic ratio of bismuth ions to tin ions is 5:1 to 1:1, preferably 4:1 to 2:1, more preferably 3.5:1 to 2.5:1, based on the total number of atoms in the bismuth and tin ion solutions. In one or more embodiments, the process for producing the metal oxide support comprises adding an ammonia solution to the bismuth-tin ion solution, heating, autoclaving the formed gel, vacuum drying, and calcining. The sol-gel is then doped with a palladium solution, a PEG template is added, and the material is filtered, washed with distilled water several times, dried, and calcined.

In one embodiment, the sol-gel was formed by reacting a 1-25%, preferably 10-20% ammonia solution with the bismuth and tin ion solutions at 50-100° C. As used herein, calcination refers to a thermal treatment process in the presence of air or oxygen that is applied to solid materials to bring about a thermal decomposition, phase transition, or removal of a volatile fraction. In one embodiment, the catalyst is calcined at 300-700° C., preferably 400-600° C., more preferably 475-525° C. Raman spectroscopy is a technique used to observe vibrational, rotational, and other low-frequency modes in a system. It can therefore be used to decipher the orientation of crystalline phases. In terms of the present invention, calcining the catalyst at elevated temperatures was determined to cause a phase shift of the bismuth oxide phase from $\alpha$-$Bi_2O_3$ to $\beta$-$Bi_2O_3$, as indicated by an intensity enhancement of $\beta$-$Bi_2O_3$ (100 cm$^{-1}$), and loss $\alpha$-$Bi_2O_3$ (210 cm$^{-1}$) phase.

The present invention relates to a method of reacting an oxidant and a hydrocarbon under ultraviolet irradiation in the presence of the metal oxide supported palladium catalyst.

In the present invention, polycyclic aromatic hydrocarbons are defined as organic molecules comprised of mostly carbon and hydrogen, which contain multiple aromatic rings. These structures may or may not contain branching elements off of the aromatic rings, and may also contain fused aromatic rings. In one embodiment, the hydrocarbon is fluorene, and the reacting forms a mixture comprising fluorenol/fluorenone oxidation products. In another embodiment, the photochemical oxidation reaction generates byproducts each comprising less than 5%, preferably less than 2%, more preferably less than 1% of the total product yield. Examples of the degradation byproducts of fluorene oxidation include, but are not limited to dibenzofuran and phthalic anhydride.

In one embodiment, the oxidant is molecular oxygen. The metal oxide supported palladium catalyst and fluorene are dispersed in a solvent, purged with molecular oxygen, and irradiated. The molecular oxygen can either be passed through the reaction mixture prior to, or during ultra violet irradiation, preferably prior to irradiation. Molecular oxygen can be passed through the reaction mixture for 1-60 minutes, preferably 25-35 minutes, at a rate of 1-60 ml/min, preferably 25-45 ml/min, more preferably 30-40 ml/min.

Ultraviolet (UV) light is electromagnetic radiation with a wavelength shorter than that of visible light but longer than X-rays (from 400 nm to 10 nm in wavelength). In one or more embodiments, the ultraviolet radiation source is a high pressure mercury lamp with an average light intensity of 30-90 mWcm$^{-2}$, preferably 50-70 mWcm$^{-2}$, more preferably 55-65 mWcm$^{-2}$, producing ultraviolet light with a wavelength in between 320 and 400 nm. In a preferred embodiment, this mercury lamp produces wavelengths with strong emission lines at 325, 343, 365, 366 and 391 nm. In another embodiment, the high pressure mercury lamp has a power range of 50-150 W, preferably 100-135 W, more preferably 120-130 W.

In one embodiment, the catalyst loading is 50-500 mg per 350 ml of fluorene, preferably 100-300 mg, more preferably 150-250 mg, even more preferably 190-210 mg. Catalyst stability is one important factor for determining large scale catalytic process applications. In this invention, the metal oxide supported palladium catalyst can be recovered and reused in 1-10, preferably 4-6 reaction iterations.

Suitable solvents that may be used for the photooxidation process include aprotic polar solvents, polar protic solvents, and non-polar solvents. Suitable aprotic polar solvents may include, but are not limited to, propylene carbonate, ethylene carbonate, butyrolactone, acetonitrile, benzonitrile, nitromethane, acetonitrile, nitrobenzene, sulfolane, dimethylformamide, N-methylpyrrolidone, or the like. Suitable polar protic solvents may include, but are not limited to, water, nitromethane, and short chain alcohols. Suitable short chain alcohols may include, but are not limited to, one or more of methanol, ethanol, propanol, isopropanol, butanol, or the like. Suitable non-polar solvents may include, but are not limited to, cyclohexane, octane, heptane, hexane, benzene, toluene, methylene chloride, carbon tetrachloride, or diethyl ether. Co-solvents may also be used. Exemplary solvents include acetonitrile.

In photocatalytic processes, the active radical species that are generated following irradiation can be quenched with active species scavengers. In one embodiment, suitable modifiers may include, but are not limited to, one or more of isopropanol, p-benzoquinone, and triethanolamine. These active species scavengers can be added to attenuate the reactivity of the metal oxide supported palladium catalyst. In one embodiment, the amount of modifier present may be between 0.1-3 mM, preferably 0.5-2 mM, more preferably 0.8-1.2 mM.

The examples below are intended to further illustrate protocols for preparing, characterizing metal oxide supported palladium catalyst, and uses thereof, and are not intended to limit the scope of the claims.

EXAMPLE 1

Synthesis of Pd/$SnO_2$—$Bi_2O_3$ Nanostructures

All chemicals were analytical grade and used without further purification. In a typical procedure, appropriate amounts of $Bi(NO_3)_3.5H_2O$ and $Sn(NO_3)_4$ were used so as to obtain a 3:1 atomic ratio in the final product. $Bi(NO_3)_3.5H_2O$ was first dissolved in water containing polyethylene glycol-2000 [(HO($CH_2CH_2O$)$_n$H)-PEG 2000-2 g/100 ml water)] (100 ml) and same for $Sn(NO_3)_4$. $Sn(NO_3)_4$ solution was poured onto the $Bi(NO_3)_3.5H_2O$ solution under vigorous stirring. Ammonia solution (15%) was then added into the mixed solution in a drop wise manner until precipitation takes place and thus the reacting solutions were kept at 85° C. under vigorous stirring until a gel was formed. Then, the gel was transferred into a Teflon-lined stainless autoclave (300 mL capacity) at the temperature of 140° C. for 24 h via incubation in an electric oven. The system was then cooled to ambient temperature naturally. The as-prepared sample was collected and washed with distilled water and absolute ethanol several times, vacuum-dried, and then calcined at 500° C. for 6 h to obtain $SnO_2$—$Bi_2O_3$ nanostructures. This sample was denoted as SnBi3$_{SG}$ where 3 accounts for the atomic ratio of 3/1 (Bi/Sn) and SG is accounted for the sol-gel method of preparation. Palladium nitrate Pd($NO_3$)$_2$ at a weighing of 2% is taken as starting material to dope the SnBi3$_{SG}$ material, which has been dissolved in distilled water forming an emulsion using a ball mill. After mixing, PEG 6000 at a concentration of 3 g/100 ml was added step-wisely to the mixture for sake of Pd ions reduction. The mixture was left for one day under stirring, filtering and washing with distilled water for several times. Then, dried at 110° C. for 5 h and calcined at 500° C. for 6 h. This sample was denoted as Pd/SnBi3$_{SG}$.

EXAMPLE 2

Synthesis of Pd/$Bi_2O_3$ Nanostructures

In a typical procedure, a stoichiometric amount of $Bi(NO_3)_3.5H_2O$ was dissolved in 100 ml of distilled water containing polyethylene glycol-2000. The pH was adjusted to a value of 8.8 via drop-wise addition of ammonia solution (15%, v/v) was performed until complete precipitation. After gelation for 24 h in a Teflon lined autoclave at 140° C., the gel was then filtered, washed with distilled water for several times and dried at 110° C. overnight. Finally, the sample was calcined at 500° C. for 6 h. To a portion of the calcined sample, an adequate amount of Pd($NO_3$)$_2$ solution; so as to form a loading of 2% Pd, was added. Subsequently, vigorous stirring was achieved followed by drop-wise addition of PEG-6000 at a concentration of 3 g/100 ml. Calcinations at 500° C. for 6 h was accomplished following filtering, washing and drying at 110° C. This sample was denoted as Pd/Bi$_{SG}$.

EXAMPLE 3

X-Ray Diffraction (XRD)

The X-ray powder diffraction patterns of various solids were carried out using a Philips 321/00 instrument. The patterns were run with Ni-filtered Cu Kα radiation (λ=1.541 Å) at 36 kV and 16 mA with scanning speed of 2° in 2θ min$^{-1}$. The XRD phases present in the samples were identified with the help of ASTM powder data files.

EXAMPLE 4

N$_2$ Adsorption

The surface properties namely BET surface area, total pore volume (Vp) and mean pore radius (r) were determined from N$_2$ adsorption isotherms measured at 77 K using conventional volumetric apparatus. The samples were outgassed at 473 K for 3 h under a reduced pressure of 10$^{-5}$ Torr before starting the measurement. The total pore volume was taken from the desorption branch of the isotherm at p/p$^0$=0.98, assuming complete pore saturation.

EXAMPLE 5

Ultraviolet-Visible Diffuse Reflectance Spectroscopy

Diffuse Reflectance Ultraviolet-visible spectroscopy (UV-vis DRS) of powder samples was carried out at room temperature using a PerkinElmer Lamda-900 spectrophotometer in the range of 200-800 nm. The UV-vis spectra were processed with Microsoft Excel software, consisting of calculation of the Kubelka-Monk function, F(R$_\infty$), which was extracted from the UV-vis DRS absorbance. The edge energy (E$_g$) for allowed transitions was determined by finding the intercept of the straight line in the low-energy rise of the plot of [F(R$_\infty$)hV]$^2$, for the direct allowed transition, vs hV, where hV is the incident photon energy

EXAMPLE 6

Transmission Electron Microscope (TEM)

TEM micrographs were measured using a Philips; model Tecani Feil2, at an accelerating voltage of 200 KV. The powder samples were put on carbon foil with a microgrid. TEM images were observed with minimum electron irradiation to prevent damage to the sample structure. The elemental compositions of the composite material were investigated by energy-dispersive X-ray attached to the TEM equipment. The average particle diameter (d) was calculated by the following formula: d=Σnidi/Σni, where ni is the number of particle diameter di in a certain range, and Σni is more than 100 particles on TEM images of the sample. Computer-assisted counting of nanoparticle images and automated image analysis based software package including KONTRON KS 400 (Zeiss-Kontron) was used.

EXAMPLE 7

Raman Spectroscopy

Raman spectroscopy was used to characterize the observed various phases. The LabRam HR is an integrated and compact Raman system. It is composed of a Helium Neon laser source, a confocal microscope coupled to a 800 mm focal length achromatic spectrograph and a two-dimensional multichannel CCD. The excitation wavelength of the internal 17 mW HeNe laser is 632.8 nm. An additional entrance for one or more external lasers is available in the basic version of the system. The integrated microscope is a high stability BX41 frame from Olympus. It incorporates white light both by reflection and by transmission. A video camera permits the user to control and to visualize the sample under the microscope objective and to check the position of the attenuated laser spot on this sample. The dispersive stage of the LabRAM HR is a Czerny-Turner achromatic spectrograph with a 30 mm wide flat field, optimized for a multichannel detection. This spectrograph is equipped with an automated twin grating turret offering high and low dispersion. The standard detector is a high performance TE cooled CCD detector of 1024×256 pixels (26×26 μm2). The LabSpec software which controls the parameters of the system includes advanced treatment functions for Raman spectral analysis and imaging.

EXAMPLE 8

Measurements of Photocatalytic Activity

Fluorene (98%) used in the photooxidation experiments was used as received from Acros. The photooxidation experiments were performed in a photoreactor made of quartz and equipped with a specific tubular space for the UV lamp as well as a cooling jacket. A high pressure Hg lamp (125 W) equipped with a UVA responsive to 320-400 nm; and presented strong emission lines at 325, 343, 365, 366 and 391 nm, manufactured by Vilber Lourmat, France was used as an UV light source; with an average light intensity equal 60 mWcm$^{-2}$. It placed at its specified position using a special rod in the reactor. A continuous cold water (16±1° C.) supply was maintained during the experiment to control the temperature of the reaction mixture. The 350 ml of 6×10$^{-4}$ mol fluorene; dissolved in degassed acetonitrile solution, mixed with 100 mg of the photocatalyst was stirred for 30 min to prepare a uniform dispersion of the catalysts particles at room temperature followed by passage of an oxygen current through an inlet tube for 30 min at a 35 ml/min rate. After a specified time, the oxygen current was ceased and the UV lamp was turned on. The experimental setup was completely covered with aluminum foil and samples were collected every hour for a period of 6 h for analysis using Shimadzu GC-MS-QP5050. This bench top quadrupole mass spectrometer features an extended mass range to 900 Daltons and optional positive and negative chemical ionization (PCI and NCI). Scan speeds of up to 6,750 AMU/sec were achieved with unit mass resolution. The MS was paired with GC-17A gas chromatograph, which uses Advanced Flow Control (AFC) for rapid as well as reproducible results. Ionization mode: EI, PCI, and NCI, Ionization voltage: 70 eV, Ionization current: 60 mA EI, 200 mA CI, Filament: dual, are implemented and well used. For detecting the active species [hydroxyl radicals (.OH), superoxide radical (.O$_2^-$) and holes (h$^+$)] as well as their role in the photocatalytic reaction, the following scavengers were added: 1.0 mM isopropanol (IPA—a quencher of .OH), p-benzoquinone (BQ—a quencher of $.O_2^-$), and triethanolamine (TEOA—a quencher of h$^+$). The method was similar to the former photocatalytic experiments. As reported earlier the quantum yield [P. D. Bartlett, M. E. Landis, Journal of the American Chemical Society 99:9 (1977) 3033-3037—incorporated herein by reference in its entirety] for the photooxidation process ($\phi_{ox}$) at 343 nm was then determined as follows:

$$\phi_{343} = \frac{\text{no. of molecules reacted}}{\text{no. of photons absorbed}}$$

$$\text{No. of molecules reacted} = \frac{\text{Wt.}}{\text{Mol. wt.}} \times A \times \text{yield}$$

where $A$ is Avogadro's number

No. of photons absorbed in 0.5h (exposure time) =

$$\frac{\text{Total power absorbed}}{\text{Energy of single photon at 343 nm } (hc/\lambda)}$$

(amount of light absorbed × lamp power × time/sec)

EXAMPLE 9

XRD and TEM Study

The XRD patterns of the as-prepared samples calcined at 500° C. are shown in FIG. 1. The pattern of $SnO_2$—$Bi_2O_3$ ($SnBi3_{SG}$) indicates various lines ascribed to $Bi_2O_3$ [at 2θ=24.1°, 37.2° (104), 41° (120), 43.8° (113), 48° (202), 53.2° (024), 58.5° (116)], $SnO_2$ [at 2θ=33.5° (101), 49.5° (211), 53.9° (220), 55.4° (002)] and $Bi_2Sn_2O_7$ [at 32.5°, 35° (331)] [Y. Xiong, J. Chen, B. Wiley, Y. Xia, Y. Yin, Z. Y. Li, Nano letters, vol. 5 No. 7 (2005) 1237-1242—incorporated herein by reference in its entirety]. The XRD pattern of the Pd/SnBi3$_{SG}$ sample demonstrated apart from the existed lines ascribed to $Bi_2O_3$ [at 2θ=24.1°, 48° (202), 53.2° (024)], the disappearance of some others related to the same species [at 2θ=37.2° (104), 41° (120), 43.8° (113), 58.5° (116)]. New peaks at 2θ=31.5° and 32.1° corresponding to the diffraction lines of (002) and (220) planes of the tetragonal β-$Bi_2O_3$ were also shown [L. Bourja, B. Bakiz, A. Benlhachemi, M. Ezahri, J. C. Valmalette, S. Villain, J. R. Gavarri, J. Taibah University for Science 4 (2010) 1-8—incorporated herein by reference in its entirety]. On the other hand, the recognized well crystallized $SnO_2$ lines shown in SnBi3$_{SG}$ were almost vanished in Pd/SnBi3$_{SG}$. Accordingly, the solubility of $SnO_2$ in $Bi_2O_3$ produces high $Bi_2Sn_2O_7$ concentration as confirmed by exposing typical peaks at 2θ=28.8°, 33.1°, 48.1° and 57.5° [D.-W. Yuan, R.-F. Yan, G. Simkovich, J. Mater. Sci. 34 (1999) 2911-2918—incorporated herein by reference in its entirety], beside those mentioned before in the SnBi3$_{SG}$ sample and ascribed to the same phase. However, a marked decrease in crystallinity is indicated in the Pd containing sample as well as a peak broadening proposing a decrease in crystallites size of this particular sample comparatively. Accordingly, it can be suggested that $Bi_2Sn_2O_7$ was synthesized at the expense of vanishing $SnO_2$ as well as partial of $Bi_2O_3$ phases, those did not nullify the existence of other lines due to β-$Bi_2O_3$ never seen before. Of particular interest, the formation of the $Bi_2Sn_2O_7$ phase at such low temperature highlights the effect of template and hydrothermal conditions on the nucleation of this phase. The XRD pattern showed additional small intensity peaks at 2θ=40° and 47° ascribable to (111) and (200) planes of deposited Pd nanoparticles [R. Nie, J. Shi, W. Du, Z. Hou, Applied Catalysis A: General 473 (2014) 1-6—incorporated herein by reference in its entirety] as compared to the pattern of SnBi3$_{SG}$. These peaks are indexed to face-centered cubic Pd (Joint Committee on Powder Diffraction Standards (JCPDS) Card No. 05-0681, a=3.889 Å). The XRD pattern of the as-prepared Pd/Bi$_{SG}$ calcined at 500° C. using the precursors at the hydrothermal temperature of 140° C. is indexed to tetragonal crystallized β-$Bi_2O_3$ structure (PDF NO. 27-50) with major peaks at 2θ=31.76°, 32.69°, 46.22°, 54.27°, 55.48° and 57.75° corresponding respectively, to the diffractions of (002), (220), (222), (203), (421) and (402). However, residual α-$Bi_2O_3$ was also appeared (PDF NO. 6-294) with a major peak at 2θ=25.75° corresponding to the diffraction of the (002) plane of the monoclinic structure [J.-Y. Xia, M.-T. Tang, C. Cui, S.-M. Jin, Y.-M. Chen, Trans. Nonferrous Met. Soc. China 22(2012) 2289-2294—incorporated herein by reference in its entirety]. This proposes the stability of β-$Bi_2O_3$ over α-$Bi_2O_3$ following calcining at 500° C. However, it has been acknowledged by many authors that metastable β-$Bi_2O_3$ changed gradually into α-$Bi_2O_3$ as the hydrothermal temperature increased [T.-C. Kuo, Y.-L. Kuo, W.-C. J. Wei, Journal of the European Ceramic Society 31 (2011) 3153-3158—incorporated herein by reference in its entirety]. This highlights that the adopted procedure is succeeded in obtaining a more stabilized phase for the former than that of the latter. A small peak due to Pd nanocrystallite was observed at 2θ=47° (200).

Figure 2A:
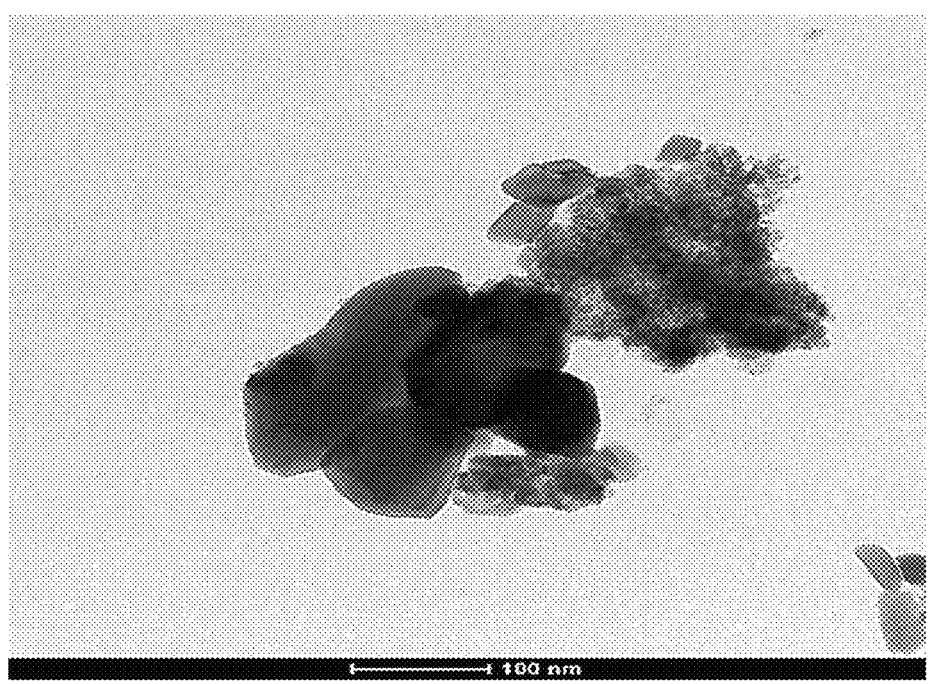
FIG. 2A is an illustration of a TEM image of $SnBi3_{SG}$.
Figure 2B:
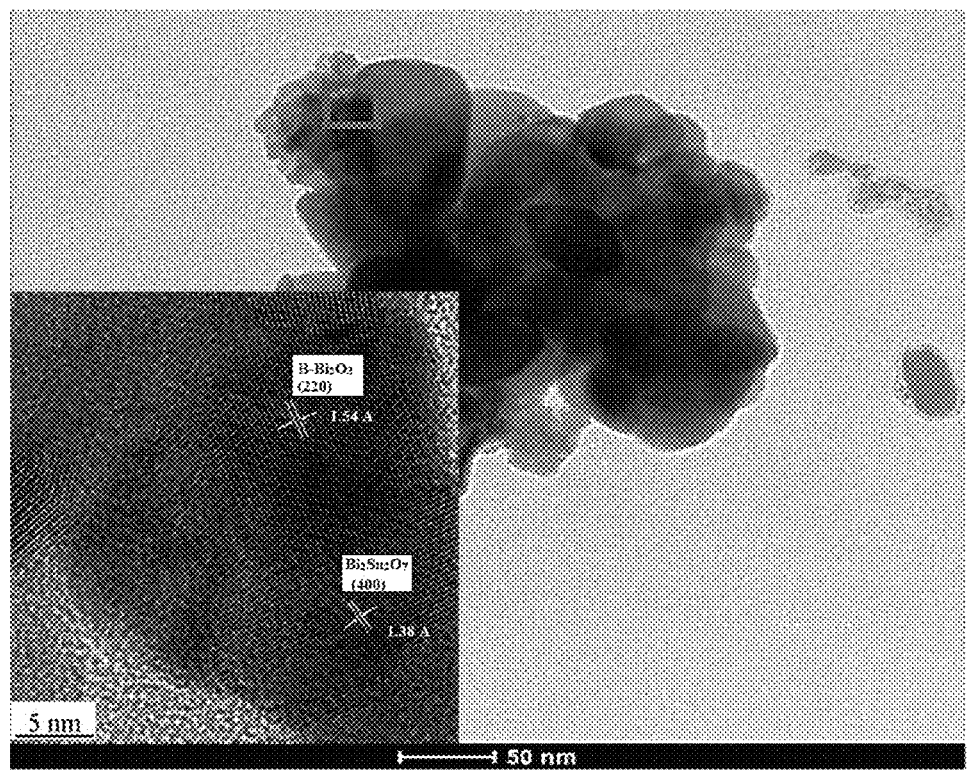
FIG. 2B is an illustration of a TEM image of $Pd/SnBi3_{SG}$ wherein the inset figure is the magnification of the shaded boxed area.
Figure 2C:
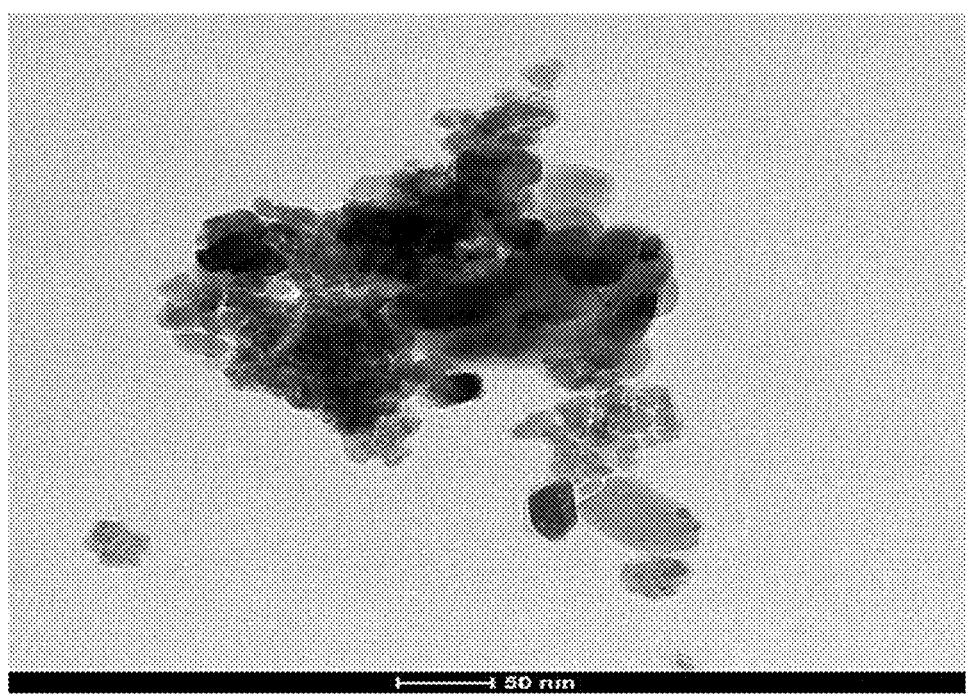
FIG. 2C is an illustration of a TEM image of $Pd/Bi_{SG}$.

The morphologies of synthesized samples were examined by TEM. The TEM image of SnBi3$_{SG}$ shows irregular polygonal crystalline structure composed of tetragonal and hexagonal shapes with average sizes of 72±1 nm (FIG. 2A). This image also shows an amorphous area in close proximity to the crystalline one with no agglomeration seen in this micrograph. The TEM image of Pd/SnBi3$_{SG}$ shown in FIG. 2B revealed a nanoplates-like structure with an average size of 44±2 nm. The HRTEM image of the nanoparticles (seen as an inset) displayed resolved lattice fringes of 1.54 Å and 1.38 Å that indexed to (220) and (400) planes of β-$Bi_2O_3$ and $Bi_2Sn_2O_7$, respectively. This indicates the close proximity of crystallized β-$Bi_2O_3$ and $Bi_2Sn_2O_7$ phases. This close interconnection between the two phases is supposed to favor the photoinduced electrons transfer between the phases that assume to reduce the recombination of the photo-induced electrons and holes, and improve the photocatalytic activity of the catalysts. The TEM image of Pd/Bi$_{SG}$ (FIG. 2C) shows irregular crystalline nano-flakes structure with average sizes of 20±2 nm. Besides, an amorphous area is depicted at the left of the image. Decreasing the particle size of this sample comparatively explains the role of the PEG template in slowing the nucleation rate via the sol-gel technique; compared with Pd/SnBi3$_{SG}$ however resulted in non-homogeneous nucleation so as to producing such irregular flaky structure.

EXAMPLE 10

Surface Texturing Study

Figure 3A:
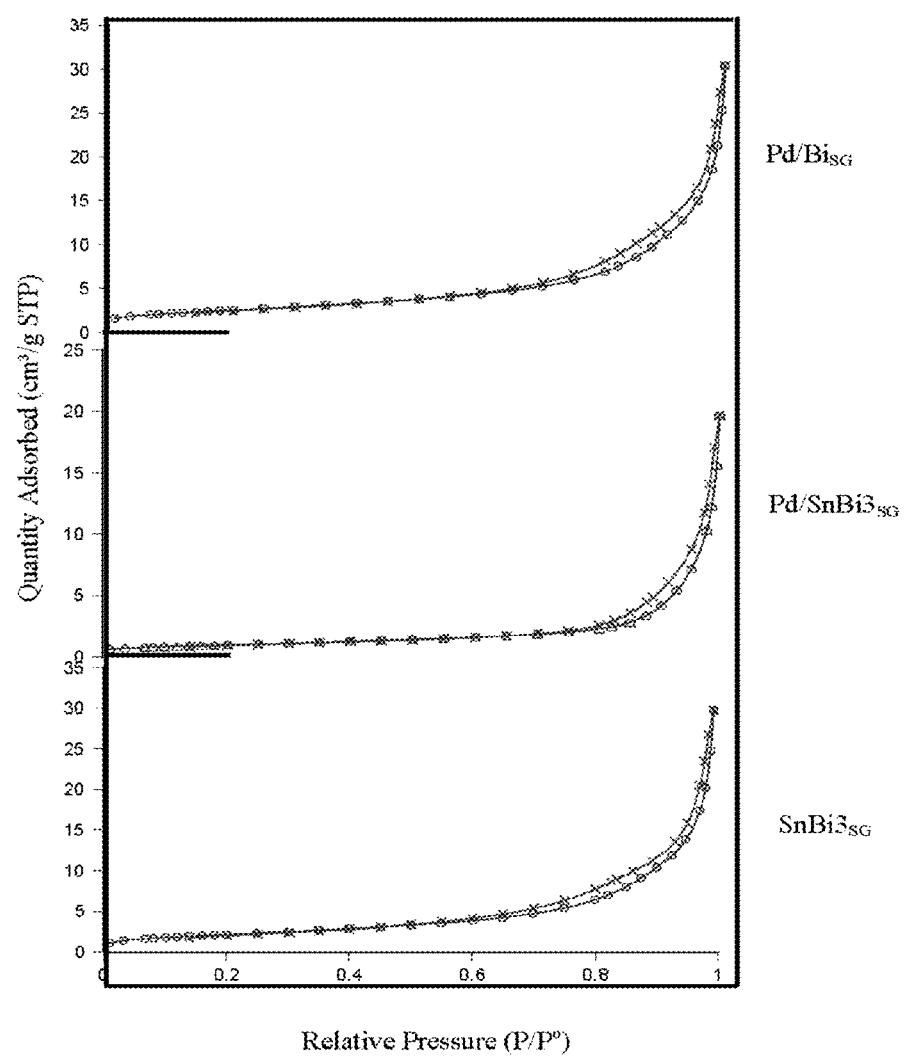
FIG. 3A is a graph illustrating adsorption-desorption isotherms.
Figure 3B:
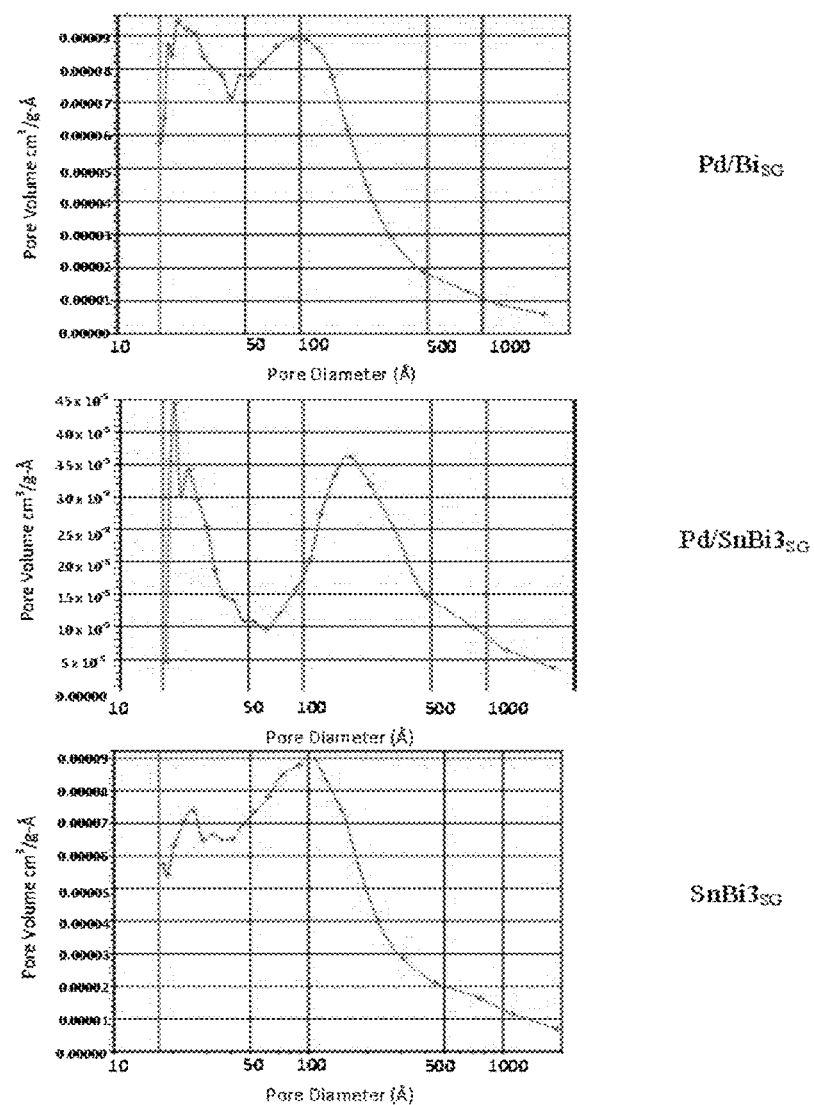
FIG. 3B is a graph illustrating the corresponding pore size distribution curves of $SnBi3_{SG}$, $Pd/Bi_{SG}$ and $Pd/SnBi3_{SG}$.

Full nitrogen sorption isotherms of synthesized samples were measured to obtain information about surface texturing properties (FIG. 3A). It can be seen that a nearly linear correlation between the absorbed volume and relative pressure is observed; under the low pressure, in the relative pressure (P/P°) range of 0-0.6, which is ascribed to unrestricted monolayer-multilayer adsorption. The sorption isotherms of the samples can be classified as type II, according to IUPAC classification and also exhibit H3-type hysteresis loops characteristic of typical mesoporous material consisting of slit-shaped capillaries. The large rise of nitrogen adsorption-desorption isotherms in the relative high pressure (P/P°) range of 0.8-1.0 is characteristic of mesoporous structure originated from the nanoporous walls or the textural mesopores with quite assembled clusters [M. M. Mohamed, M. S. Al-Sharif, Applied Catalysis B: Environmental 142-143 (2013) 432-441—incorporated herein by reference in its entirety]. The specific surface area of the SnBi3$_{SG}$ sample was calculated to be 20.8 m$^2$ g$^{-1}$ as determined by the BET equation. The corresponding Barrett Joyner Halenda (BJH) analyses derived from the absorption branch of the isotherm exhibit that most of the pores fall into the size range from 2 to 50 nm. These pores presumably arise from the spaces among the oxides composite. However, the specific surface area of the Pd/SnBi3$_{SG}$ nanostructures was calculated to be 12 m$^2$ g$^{-1}$, which is lower than that of Pd free sample proposing the inclusion of Pd nanoparticles deep inside the composite pores. As a confirmation, the desorption step in Pd/SnBi3$_{SG}$ was at P/P°=0.73 where it was at 0.6 for SnBi3$_{SG}$ reflecting the localization of Pd nanoparticles inside the pores and as a result the pore volume suffers a significant decrease (0.1564 cm$^3$/g-Å Pd/SnBi3$_{SG}$) when compared with the latter (0.2041 cm$^3$/g-Å SnBi3$_{SG}$). The Pd/SnBi3$_{SG}$ sample showed a trimodal distribution centered at 2.2 nm and 2.7 nm together with a broad one centered at 20 nm. On the other hand, the Pd/Bi$_{SG}$ sample presented an average surface area of 21 m$^2$g$^{-1}$ with a bimodal pore size distribution centered at 3 nm and 10 nm revealing the existence of a lower margin of mesopores compared with the other two samples. All the samples presented similar adsorption-desorption isotherm except that narrowing parts of the mesoporous channels and creating ink-bottle like sections were discerned in the Pd/SnBi3$_{SG}$ sample as ascertained via involving trimodal distributions upon employing the PEG template. This could be due to depositing Pd and/or one of the oxides in the pore structure of the formed SnBi3$_{SG}$ phase; most probably SnO$_2$ as ascertained from XRD, and thus creating such small distributions.

EXAMPLE 11

Optical Properties Study

Figure 4:
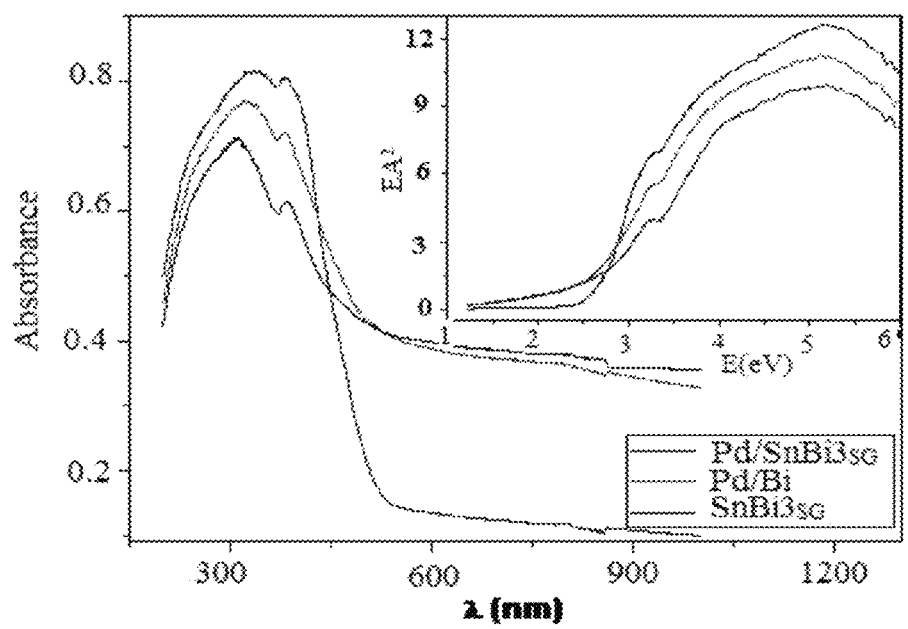
FIG. 4 is a graph illustrating UV-Vis diffuse reflectance spectra of $SnBi3_{SG}$, $Pd/Bi_{SG}$ and $Pd/SnBi3_{SG}$ and the inset is the corresponding Energy gap (Eg) values.

The optical absorption of synthesized nanostructures was measured by UV-Vis diffuse reflection spectroscopy and the results were shown in FIG. 4. The absorbance edge of the as-prepared samples was located approximately in the wavelength range from 450 to 600 nm. A significant increase in the absorption at wavelengths shorter than 450 nm for SnBi3$_{SG}$ and Pd containing samples was assigned to the intrinsic band gap absorption of SnO$_2$ and Bi$_2$O$_3$ [A. Hameed, T. Montini, V. Gombac, P. Fornasiero J. Am. Chem. Soc. 130 (2008) 9658-9659—incorporated herein by reference in its entirety]. The sample Pd/Bi$_{SG}$ has the strongest absorption probably due to surface roughness rather than the belief it was due to increasing the particles size [J. Wu, F. Huang, X. Lu, P. Chen, D. Wan, F. Xu, J. Mater. Chem. 21(2011) 3872-3876—incorporated herein by reference in its entirety]. Because this sample showed the lowest crystallite size as observed by TEM. The intensity of absorption is increased for Pd containing samples and even exhibit a red shift for the 337-350 nm band apart from the corresponding Pd free mixed oxide one (SnBi3$_{SG}$-325 nm). This implies an increase in the absorption edge of Pd containing catalysts towards longer wavelengths, proposing a decrease in their particles size; as confirmed using the XRD and TEM results. The absorption edge of latter samples acquired an additional shift in the visible light region compared to SnBi3$_{SG}$. The band gap energies of the as-prepared Pd/SnBi3$_{SG}$ and Pd/Bi$_{SG}$ were determined from the plot of (ahv)$^2$ vs energy (hv) (the inset in FIG. 4) and were found to be at 2.10 and 2.0 eV, respectively. Whereas, the band gap of SnBi3$_{SG}$ heterostructures was found to be 2.4 eV. Such differences may be ascribed to the changes in crystalline phase and defects might be created following Pd incorporation [L. Zhang, W. Wang, J. Yang, Z. Chen, W. Zhang, L. Zhou, S. Liu, Applied Catalysis A: 308 (2006) 105-110—incorporated herein by reference in its entirety]. Furthermore, transforming part of oxide phases; as depicted from XRD results, permanently from SnO$_2$ and Bi$_2$O$_3$ to Bi$_2$Sn$_2$O$_7$ leads to a decrease in the band gap [A. Hameed, T. Montini, V. Gombac, P. Fornasiero J. Am. Chem. Soc. 130 (2008) 9658-9659—incorporated herein by reference in its entirety]. Optical characterization of nanocrystallites Bi$_2$O$_3$ and SnO$_2$ synthesized individually using some other methods indicate higher band gap values (2.85-2.8 eV) [F. Pourfayaz, A. Khodadadi, Y. Mortazavi, S. S. Mohajerzadeh, Sensors & Actuators B: 108 (2005) 172-179—incorporated herein by reference in its entirety]. This highlights that the formation of Bi$_2$Sn$_2$O$_7$; based on the involvement of SnO$_2$ in the structure of Bi$_2$O$_3$, besides the adopted hydrothermal method used in synthesizing this nanocomposite could have a positive impact towards decreasing band gap values. On the other hand, no special surface Plasmon peak was noticed for Pd doped SnBi3$_{SG}$ and bismuth (used to be at 390-420 nm) probably due to the well-dispersion of Pd nanoparticles; of low amount, and to the presence of isolated energy levels in the band gap of the semiconductor [P. Maruthamuthu, M. Ashokkumar, Solar Energy Mater. 17(1988) 433-439—incorporated herein by reference in its entirety] composite. Accordingly, the peak at 410 nm cannot be assigned to surface Plasmon resonance of Pd nanoparticles since it appeared in the Pd free SnBi3$_{SG}$ sample.

EXAMPLE 12

Raman Study

Figure 5A:
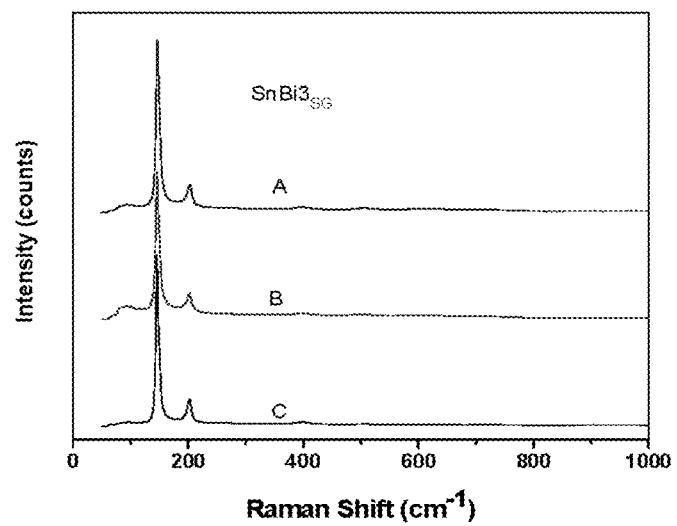
FIG. 5A is a graph illustrating the Raman spectra obtained for $SnBi3_{SG}$ sampled at three different locations A-C, at room temperature with vibration frequencies between 0 and 1000 $cm^{-1}$, together with FIG. 5B.
Figure 5B:
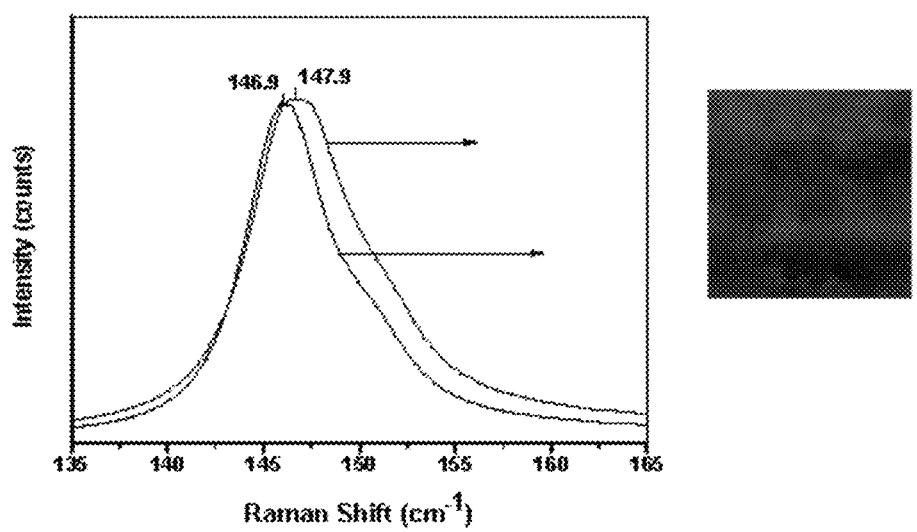
FIG. 5B is a graph illustrating the mapping spectra obtained in the 146-148 $cm^{-1}$ margin.

The spectra of the SnBi3$_{SG}$ material measured at 3 different positions presented fairly similar information (FIG. 5A). The Raman bands at 90 and 520 cm$^{-1}$ are associated to the tetragonal phase of β-Bi$_2$O$_3$ whereas 146 and 210 cm$^{-1}$ are due to monoclinic phase of α-Bi$_2$O$_3$ [Narang S. N., Patel N. D., Kartha V. B., Journal of Molecular Structure 327 (1994) 221-227—incorporated herein by reference in its entirety]. The new band at 390 cm$^{-1}$; which never seen in either tetragonal β or monoclinic α structures, could characterize the Bi$_2$Sn$_2$O$_7$ structure; in concordance with XRD results of SnBi3$_{SG}$. To have a better overview of the homogeneity, an area of the sample was mapped (70×75 μm) (FIG. 5B). Although all the spectra of the map are looking similar, small shifts in peak positions are observed at 146.9 and 147.9 cm$^{-1}$ over the whole map. This slight difference was indicative to the sample heterogeneity. Accordingly, this might be due to slight changes in the particle size within the sample. It has been reported in the literature that Raman bands shift toward higher wavenumbers as the particle size decreases [D. H. Franklin, I. E. Wachs, Journal of Solid State Chemistry 97 (1992) 319-325—incorporated herein by reference in its entirety].

Figure 5C:
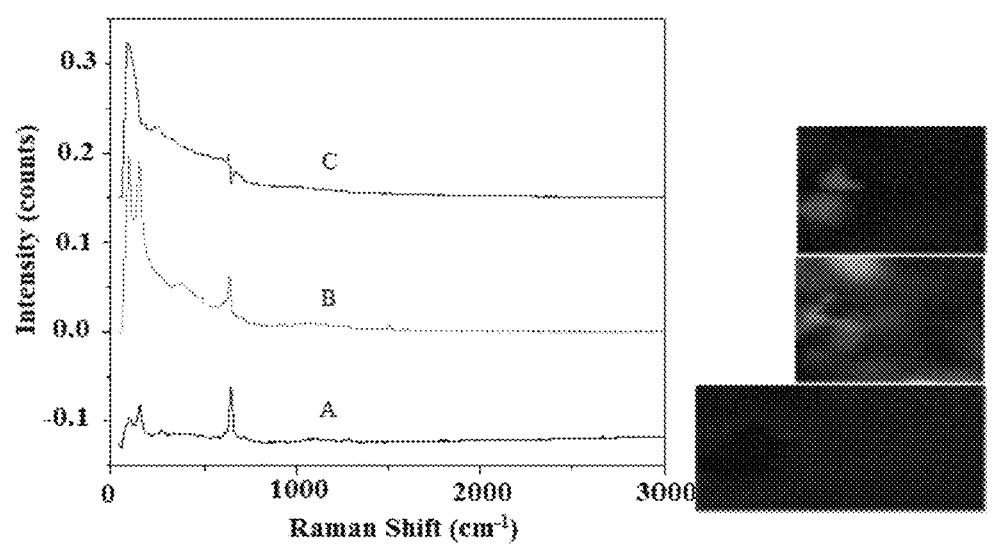
FIG. 5C is a graph illustrating the Raman and mapping spectra of $Pd/Bi_{SG}$ sampled at three different locations A-C, with the vibration frequencies between 0 and 500 $cm^{-1}$.

The Raman spectrum of Pd/Bi$_{SG}$ measured at three different locations is depicted in FIG. 5C. For this sample, three factors are used to describe the dataset, each of them expressing some variation. In order to find out the different sources of variance in the map dataset, the MCR algorithm is applied. Three MCR factors (or loadings) are used to describe the dataset; each individual spectrum of the map is a combination of the MCR factors altered by scores (coefficients where scores are displayed as maps). The first spectrum (A) presents peaks centered at 100 and 307 cm$^{-1}$ assigned to the β-Bi$_2$O$_3$ (tetragonal) phase whereas that at 210 cm$^{-1}$ is attributed to the α-Bi$_2$O$_3$ (monoclinic) phase [Narang S. N., Patel N. D., Kartha V. B., Journal of Molecular Structure 327 (1994) 221-227—incorporated herein by reference in its entirety]. The Raman peak of the higher frequency mode 210 cm$^{-1}$ is attributed to the displacements of the 0 atoms in α-Bi$_2$O$_3$. Meanwhile, a strong peak is observed at 630 cm$^{-1}$ together with a very small one at 735 cm$^{-1}$, corresponding to γ-Bi$_2$O$_3$ nanoparticles [S. Venugopalan, A. K. Ramdas, Physical Review B: 5 (1972) 4065-4069—incorporated herein by reference in its entirety]. Mapping another area of the sample (B) indicates the intensity enhancement of the peaks assigned to β-Bi$_2$O$_3$ and α-Bi$_2$O$_3$ (100, 210 cm$^{-1}$) as well as the existence of a broad peak at 400 cm$^{-1}$ due to β-Bi$_2$O$_3$ together with the decrease in intensity of the peak positioned at 635 cm$^{-1}$. This indicates that the thermal treatment of Pd bismuth at 500° C. induces two effects: an oxidation followed by a structural transformation from the monoclinic α-Bi$_2$O$_3$ structure to major amounts of tetragonal β-Bi$_2$O$_3$ [J. Cheng, H. Xin, H. Zheng, B. Wang, Journal of Power Sources 232 (2013) 152-158—incorporated herein by reference in its entirety]. The significant Raman changes in the spectra were found in the spectrum map C; as for the strong peak appeared at 100 cm$^{-1}$ due to β-Bi$_2$O$_3$ and the disappearance of the peaks correlated to γ-Bi$_2$O$_3$ and α-Bi$_2$O$_3$; in concordance with XRD results of this sample. Indeed, these obtained results measure the heterogeneity of the sample and the obvious increasing intensity ratio of β-Bi$_2$O$_3$, comparatively. This is probably due to coating of the β-Bi$_2$O$_3$ phase and the increase of the disorder resulting from the hydrothermal reaction and Pd nanoparticles incorporation.

Figure 5D:
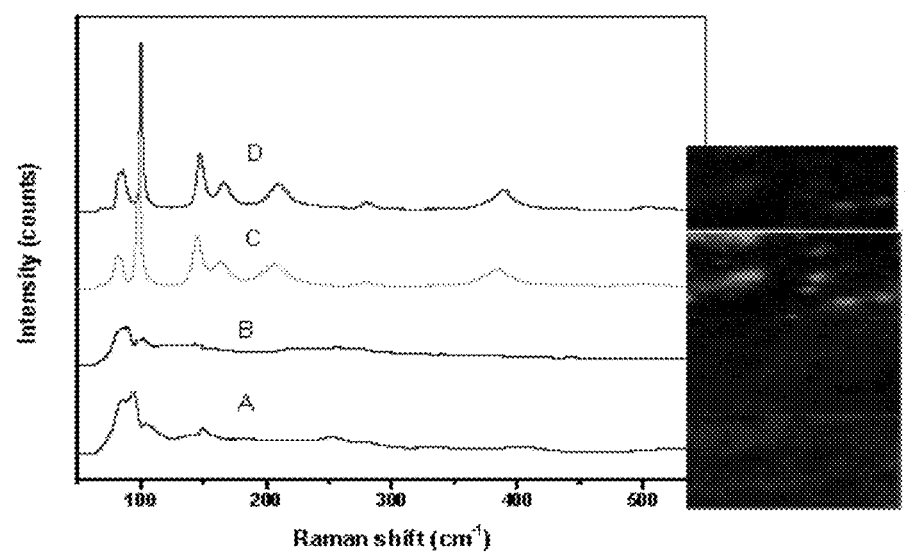
FIG. 5D is a graph illustrating the Raman and mapping spectra of $Pd/SnBi3_{SG}$ sampled at four different locations A-D, with the vibration frequencies between 0 and 500 $cm^{-1}$.

In order to find out the different sources of variance in the map dataset, the MCR algorithm is applied for the Pd/SnBi3$_{SG}$ sample (FIG. 5D). Four MCR factors (or loadings) are used to describe the dataset; each individual spectrum of the map is a combination of the MCR factors altered by scores (coefficients). As observed in the Pd/Bi$_{SG}$ sample, the different factors indicate the heterogeneity of the sample. Here, MCR factors one (D) and two (C) look similar; however all peaks are shifted of about 1-2 cm$^{-1}$, in a similar way as observed for the SnBi3$_{SG}$ sample (with potentially the same reasons explaining these shifts into slight chemical changes or particle size dependence). In this response, a doublet peak in the range 60-80 cm$^{-1}$ together with small ones at 100 cm$^{-1}$ and 150 cm$^{-1}$ were discerned. These Raman phonons are associated to the tetragonal phase of β-Bi$_2$O$_3$ [D. J. Arenas, L. V. Gasparov, W. Qiu, J. C. Nino, C. H. Patterson, D. B. Tanner, Phys. Rev. B 82 (2010) 214302-214308—incorporated herein by reference in its entirety]. Some other broad modes appeared at 255, 280, 405 and 540 cm$^{-1}$. In this region of the spectrum, such modes were assigned by comparison to infrared active modes to related pyrochlores [M. H. Chen, D. B. Tanner, J. C. Nino, Phys. Rev. B: 72 (2005) 54303-54309; H. Wang, S. R. Foltyn, Q. X. Jia, P. N. Arendt, X. Zhang, J. Appl. Phys. 100 (2006) 053904-053909; M. Fischer, T. Malcherek, U. Bismayer, P. Blaha, K. Schwarz, Phys. Rev. B: 78 (2008) 014108-014112—each incorporated herein by reference in its entirety], i.e. Raman active bands obtained for Bi$_2$Sn$_2$O$_7$. Accordingly, we assigned the modes observed at 255, 405 and 540 cm$^{-1}$ as being due to the O—Sn—O bending, O motion in SnO$_6$ polyhedra (F$_{2g}$) and the O-vacancy stretching (A$_{1g}$), respectively. Whereas the peak at 280 cm$^{-1}$ was due to α-Bi$_2$O$_3$ [S. Brown, H. C. Gupta, J. A. Alonso, M. J. Martinez-Lope, Phys. Rev. B: 69 (2004) 054434-054439—incorporated herein by reference in its entirety]. The latter modes together with that at 150 cm$^{-1}$ were almost vanished in spectrum B due to sample heterogeneity. Factors three (B) and four (A) showed different features and express other source of variation within the dataset. They might not correspond to pure material spectra but account for some of the spectral variations of the map due to chemical and/or structural changes within the sample. Accordingly, spectra C and D almost showed typical peaks at 65-75 cm$^{-1}$ as a doublet, 100s, 145, 170, 230, 274, 382 and 475 cm$^{-1}$. The Raman phonons observed until wavenumbers equal 100 cm$^{-1}$ were typical of those seen in spectrum A. Raman phonons observed at 145 and 170 cm$^{-1}$ were assigned to O—Bi—O bending (F$_{1u}$) and α-Bi$_2$O$_3$, respectively [H. C. Gupta, S. Brown, N. Rani, V. B. Gohel, Int. J. Inorg. Mater. 3 (2001) 983-990—incorporated herein by reference in its entirety]. In the intermediate region, we assigned the modes observed at 274 and 382 cm$^{-1}$ as being due to the O—Sn—O bending and Bi-0 stretching. Similar to other pyrochlores, the (F$_{2g}$) is observed at lower wavenumbers than (E$_g$) mode in this region, thus we have assigned the 230 cm$^{-1}$ modes as originating from the (F$_{2g}$) mode. The band observed at 475 cm$^{-1}$ is usually correlated to the Sn—O stretching mode [M. Maczka, J. Hanuza, K. Hermanowicz, A. F. Fuentes, K. Matsuhira, Z. Hiroi, J. Raman Spectrosc. 39 (2008) 537-543—incorporated herein by reference in its entirety].

EXAMPLE 13

Effect of Different Parameters on Oxidation Percentages

Figure 6:
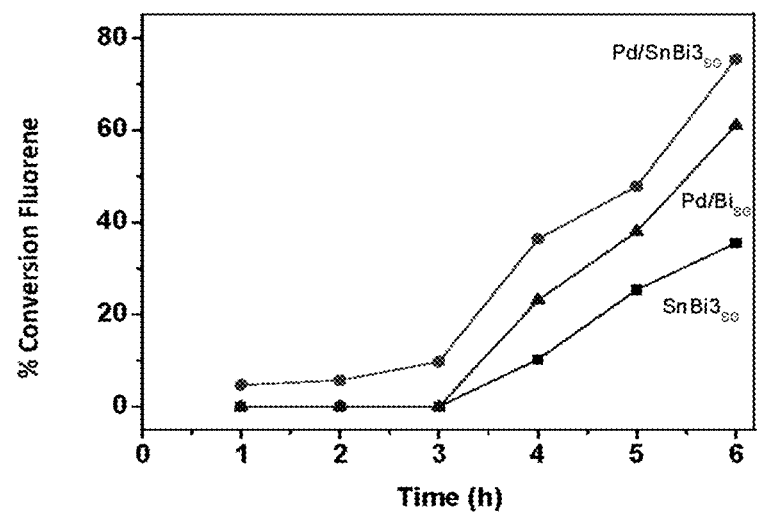
FIG. 6 is a graph illustrating conversion values of $SnBi3_{SG}$, $Pd/Bi_{SG}$ and $Pd/SnBi3_{SG}$ towards fluorene photo-oxidation (reaction conditions: fluorene concentration=$6\times 10^{-4}$ mol, catalyst weight=100 mg, time=6 h, light intensity=60 $mWcm^{-2}$, lamp pressure=125 W).

The effect of catalyst composition on fluorene % conversion is illustrated in FIG. 6. It can be seen that Pd/SnBi3$_{SG}$ enhanced significantly fluorene % conversion to 75% whereas Pd/Bi$_{SG}$ verified a conversion equal 62%, after 6 h reaction time.

Figure 7:
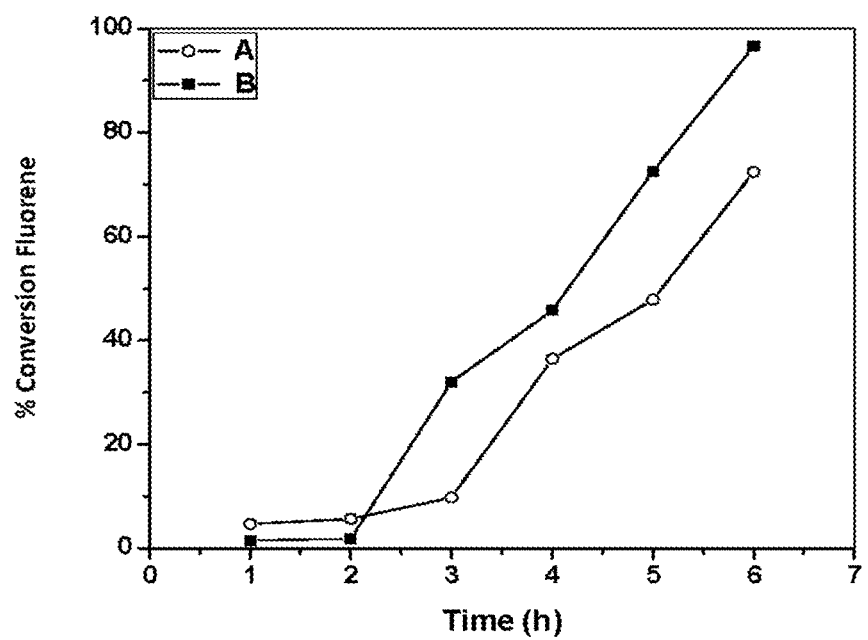
FIG. 7 is a graph illustrating the effect of $O_2$ flushing (A) during illumination and (B) prior to illumination (for 30 minutes) on the fluorene photo-oxidation activity of $Pd/SnBi3_{SG}$. Reaction conditions as in FIG. 6, except that the catalyst weight was 200 mg.

On the other hand, the Pd free sample named SnBi3$_{SG}$ indicated lower activity comparatively and revealed a conversion comprised of 35%, proposing that the active sites are due to the synergism between SnBi and Pd sites. Accordingly, the Pd/SnBi3$_{SG}$ catalyst was selected to perform subsequent reactions since it provided the highest activity. The effect of O$_2$ flushing either before or during irradiation was explored in FIG. 7. As it appears, flushing O$_2$ in advance before irradiation for 30 min shows 100% conversion compared with that done during irradiation and displayed a conversion comprised of 70%. Additionally, an induction period extending into 2 h is observed in the former case, where it enlarged to 3 h in the latter one. Apparently, flushing O$_2$ prior to illumination stimulates the semiconductor composite to form O$_2$.$^-$ species; evidenced as one of the reactive species, resulted from capturing the conduction band electrons [L. Liu, S. Tang, M. Liu, Z. Xie, W. Zhang, P. Lu, M. Hanif, Y. Ma, J. Phys. Chem. B 110(2006)13734-13740— incorporated herein by reference in its entirety]. Indeed, these photogenerated superoxide radicals cause the oxidation of all fluorene present where in case of flushing during irradiation decreases the lifetime of oxidizing species; as depicted from longer induction period, and thus decreasing its power. On the other hand, the presence of excess amounts of oxidizing species in the latter case can also oxidize the semiconductors (Sn Bi; p-n junction) into higher oxidation states by which an increase in band gap can be obtained [H. W. Kim, S. H. Shim, J. W. Lee, J. Y. Park, S. S. Kim, Chemical Physics Letters 456 (2008) 193-197—incorporated herein by reference in its entirety]. Although Pd/Bi$_{SG}$ presented slightly lower band gap energy and increased surface area values (2.0 eV and 20.8 m$^2$/g) than Pd/SnBi3$_{SG}$ (2.1 eV and 12 m$^2$/g), it presented lower activity. This was in part due to the facile transfer of electrons from β-Bi$_2$O$_3$ to Bi$_2$Sn$_2$O$_7$; in Pd/SnBi3$_{SG}$, because of their close contact as depicted from TEM results, and thus hindering charges recombination. Besides, the surface roughness depicted in Pd/Bi$_{SG}$ affected the absorption; as illustrated in TEM results and confirmed via UV-Vis diffuse reflectance findings, and thus undergoing into enough emission for stimulating electron-hole production was slightly ceased. No one can deny the influence of SnO$_2$ in the photo-oxidation process of Pd/SnBi3$_{SG}$ decisively in leading to the formation of Bi$_2$Sn$_2$O$_7$ that played a unique role in the reaction. Indeed, Raman spectra confirmed the latter result and indicated the existence of the transition mode O—Sn—O within the bulk structure of Bi$_2$O$_3$. Additionally, based on the results obtained from N$_2$ sorptiometry, this sample was particularly affected by the presence of high margin of mesopores rather than surface area value. On the other hand, although the sample SnBi3$_{SG}$ presented all the phases, including Bi$_2$O$_3$, SnO$_2$ and Bi$_2$Sn$_2$O$_7$, it presented the lowest activity probably because of exposing SnO$_2$ species, the absence of Pd nanoparticles as well as increasing the average particle size (72 nm) than rest of the samples. From the electronic transitions as well as compositional point of views it was depicted via Raman that the most prominent phase was the tetragonal β-Bi$_2$O$_3$ in all samples that constituted with Bi$_2$Sn$_2$O$_7$ phase the most active sites of the reaction; as clarified in Pd/SnBi3$_{SG}$. However, there is an uncertainty for the α-Bi$_2$O$_3$ phase; that has been existed in SnBi3$_{SG}$ and Pd/Bi$_{SG}$, because it was hardly detected in the Raman spectra of Pd/SnBi3$_{SG}$, which presented 100% conversion at the optimum conditions. On the other hand, although Raman provoked the existence of γ-Bi$_2$O$_3$ phase; which never detected in XRD probably for high dispersion and decreased crystallite size and concentration, its share in the oxidation reaction is doubtful since it is never seen in Pd/SnBi3$_{SG}$ that presented the highest activity.

Figure 8:
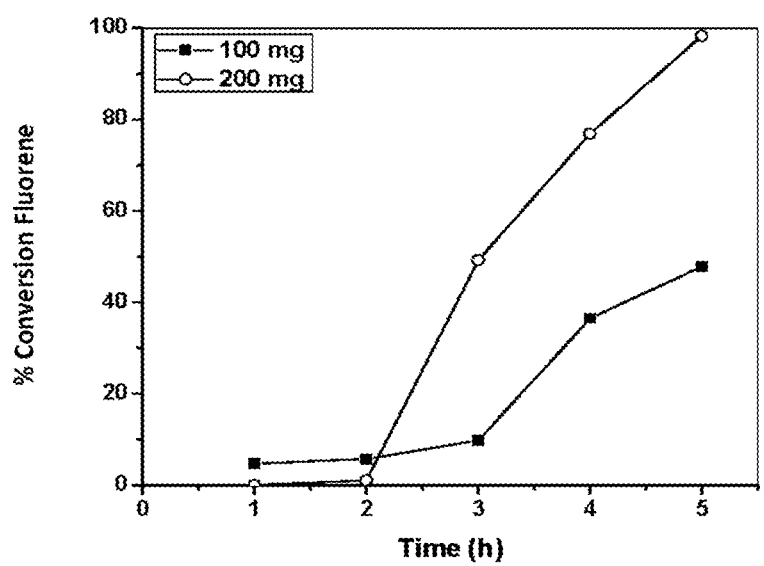
FIG. 8 is a graph illustrating the effect of catalyst weight on fluorene photo-oxidation activity of $Pd/SnBi3_{SG}$. Reaction conditions as in FIG. 6.

The effect of catalyst amount on the photocatalytic activity was then studied using two different suspensions of Pd/SnBi3$_{SG}$ (FIG. 8). Increasing the amount of the catalyst to 200 mg in the reaction mixture caused an increase in the % conversion to 100 in only 5 h. Reaching to that maximum value of the reaction yield indicates the absence of shadow effects at that concentration (200 mg). On the other hand, the decrease in conversion at 100 mg catalyst into 40% reflects the decrease in the reactive oxidizing species at that concentration. Contrarily, a marked decline in oxidation products into 20% yield was attained as the catalyst loading increased up to 300 mg (not shown). The presence of an optimum in photocatalyst concentration is quite common in this type of processes and is normally related to the potential shielding effect made by an excess of solids towards the penetrating radiation. It was observed that the fraction of fluorene adsorbed prior to illumination stage was significantly small comprised of 10% as determined via spectrophotometric analysis.

EXAMPLE 14

Effect of Different Scavengers and Identification of Oxidation Products

Figure 9:
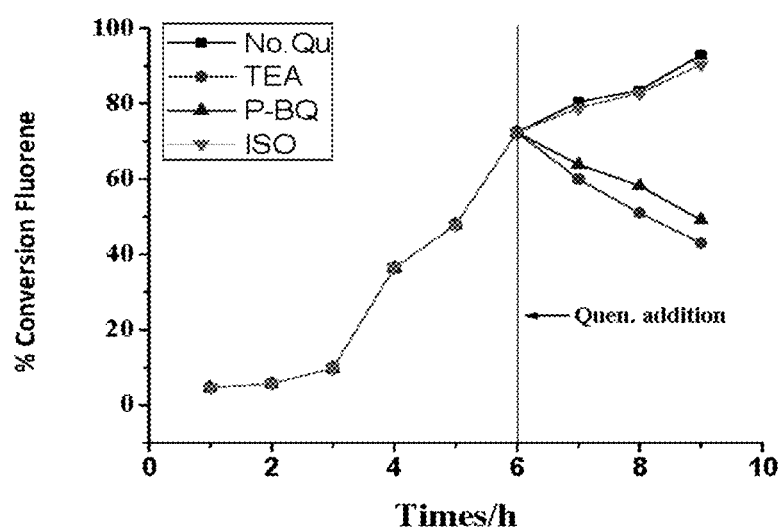
FIG. 9 is a graph illustrating the effect of different scavengers (isopropanol, IPA; p-benzoquinone, BQ; triethanolamine, TEOA) on $Pd/SnBi3_{SG}$ catalyzed fluorene photo-oxidation. Reaction conditions as in FIG. 6.

The effect of scavenging agents such as isopropanol (IPA—a quencher of .OH), p-benzoquinone (BQ—a quencher of .O$_2$$^-$, and triethanolamine (TEOA—a quencher of h$^+$) toward the photo-oxidation of fluorene was investigated under optimum conditions to investigate the active species which might exist in the photo-oxidation process [M. M. Ibrahim, S. A. Ahmed, K. S. Khairou, M. M. Mohamed, Applied Catalysis A: General 475 (2014) 90-97—incorporated herein by reference in its entirety]. As shown in FIG. 9, the presence of BQ and TEA scavengers lowered significantly the rate of photo-oxidation activity in the system. Accordingly, this revealed that holes and O$_2$.$^-$ moieties are the reactive species in the photo-oxidation reaction than that of .OH species.

TABLE 1

The percentage of the products with the synthesized photocatalysts and quantum yields calculation.

| Catalyst | Conversion % | TOF × 10$^{-6}$ S$^{-1}$ | Quantum Yield | Product Fluorenone | Selectivity Fluorenol | Dibenzofuran % | Phthalic anhydride |
|---|---|---|---|---|---|---|---|
| Pd/Bi$_{SG}$ | 100 | 9.4 | 0.03 | 55.35 | 23.56 | 7.20 | 5.80 |
| Pd/SnBi3$_{SG}$ | 100 | 9.4 | 0.1 ± .05 | 73.95 | 24.77 | 0.64 | 0.64 |
| SnBi3$_{SG}$ | 60 | 3.3 | 10$^{-2}$ | 31.26 | 12.73 | 9.51 | 6.5 |

Irradiations performed in the photochemical reactor with a 125 W lamp at 25° C., 200 mg catalyst, 5 h reaction time, 6 × 10$^{-4}$ mol fluorene; TOF = TON/Time (s) where TON = mol of products/mol of catalyst(support).
Quantum yields were calculated based on constant fluorene concentration, constant O$_2$ flushing amount as well as time and at specific wavelength and on only varied photon absorbed amount for every catalyst.

The photolysis of fluorene under UV-A radiation did show no appreciable oxidation products or elimination of the parent compound. Fluorene gave two main product peaks on a gas chromatogram obtained under our analytical condition upon using the Pd/SnBi3$_{SG}$ photocatalyst. The components of the peaks were identified as fluorenone and fluorenol as determined by the spectral database of GC/MS. The obtained data showed that fluorenone was the major product (~74%) whereas fluorenol was the minor one (~25%) accompanied with minute amounts of phthalic anhydride and dibenzofuran (see Table 1). In case of Pd/Bi$_{SG}$, the same components were formed, but at lower yield comprised of 45.35% fluorenone and 20.56% fluorenol together with appreciable amounts of phthalic anhydride and dibenzofuran exceeding those delivered using the former photocatalyst. It seems also that the composition of composites plays a significant role on the selectivity towards the products. Based on the obtained results, one can assume that increasing fluorenone/fluorenol ratio was dependent on $Bi_2Sn_2O_7$ and $\beta$-$Bi_2O_3$ heterostructures beside Pd nanoparticles. However, the decrease in this ratio as evidenced in Pd/$Bi_{SG}$ can be correlated to the absence of $Bi_2Sn_2O_7$ as well as to the decrease in the concentration of $\beta$-$Bi_2O_3$ in favor of $\alpha$-$Bi_2O_3$. On the other hand, the SnBi3$_{SG}$ sample indicates the lowest conversion comparatively (60%) and produces the least values of fluorenone (31.26%) and fluorenol (12.73%) (Table 1). As a confirmation, the TOF value of the latter sample decreases compared to the rest of samples (Table 1). Although Pd/$Bi_{SG}$ and Pd/SnBi3$_{SG}$ presented equal conversion and TOF values they displayed different selectivities. Therefore, the intrinsic activity follows a different trend. Based on the obtained results, this could probably explain the importance of $Bi_2Sn_2O_7$/$\beta$-$Bi_2O_3$ heterostructures as well as the mesoporosity of Pd/SnBi3$_{SG}$ rather than the size of crystallites that was lower in the Pd/$Bi_{SG}$ sample. Furthermore, it was confirmed that fluorenone formed by the oxidation of fluorene is very stable under light irradiation.

Light absorption of energy equal to or greater than the band gap energy of Pd/SnBi3$_{SG}$ (i.e. 2.1 eV) will result in electron ejection from the valence band to the conduction band generating a reactive electron and a positive hole: Pd/SnBi3$_{SG}$+h$\nu$→Pd/SnBi3$_{SG}$ (e$^-_{CB}$+h$^+_{VB}$). Accordingly, the electron-hole generation can be proposed to describe the resulting compounds in Table 1 and FIG. 11. The photogenerated electron can be trapped by adsorbed oxygen to form superoxide or other negatively charged adsorbed oxygen species: $O_2$+e$^-_{CB}$→$O_2.^-$. As the oxidizing power of the hole (+2.4V vs. SCE in acetonitrile) is capable of initiating single electron oxidation of an adsorbed fluorene, the fluorene radical cation can be formed which rapidly deprotonated to fluorene-hydroxyl radical. The radical intermediate is easily oxidized with the photogenerated superoxide or even with oxygen to give fluorenone/fluorenol products, as illustrated in FIG. 11. Accordingly, photocatalytic oxidation of fluorene methylene group to dibenzofuran/phthalic anhydride formation via reaction with the superoxide or with oxygen can be suggested [O. S. Mohamed, J. Photochemistry & Photobiology A: Chemistry 152 (2002) 229-232—incorporated herein by reference in its entirety]. The same mechanism was recommended by Liang and Liu [J. Chin. Chem. Soc. 32 (1986) 133-139—incorporated herein by reference in its entirety] to account for photocatalytic oxidation of diphenyl methane and by Fox et al. [J. Org. Chem. 40 (1984) 1969-1975—incorporated herein by reference in its entirety] in the case of naphthalenes. To prove that this reaction was initiated by a radical mechanism; based on the formation of $O_2.^-$, rather than singlet oxygen ($^1O_2$); that expected to be generated under similar conditions, a tetraphenylporphin sensitizer [P. D. Bartlett, M. E. Landis, Journal of the American Chemical Society 99:9 (1977) 3033-3037—incorporated herein by reference in its entirety] was added. The results indicate that the photo-oxidation was not affected accomplishing that free singlet oxygen plays no role in the current photo-oxidation reaction.

EXAMPLE 15

Quantum Yield Study

Values of quantum yield $\Phi$ for similar fluorene concentrations, oxygen content of the solvent and its dependence on amount of photons absorbed at specific wavelength are presented in Table 1. As can be seen from the data in Table 1, the quantum yield of the photo-oxidation of Pd/SnBi3$_{SG}$ is increased (0.1±0.05) and exhibited a straightforward photochemical dependent reaction, including at least one possible mechanism. That may be associated with an electron transfer process proceeding from the composite to adsorbed $O_2$ forming .$O_2^-$. On the other hand, the hole is able to initiate single electron oxidation of fluorene forming a radical cation; as mentioned previously. This mechanism is nearly dependent on the oxygen concentration (that was kept constant) and is characterized by an increase in $\Phi$ under short wavelength excitation. The values of $\Phi$ for Pd/SnBi3$_{SG}$ showed a decrease into 0.03 for Pd/$Bi_{SG}$ and $10^{-2}$ for SnBi3$_{SG}$. This highlights the weak dependence of the photo-oxidation reaction on the quantum yields of latter catalysts specifically Pd/$Bi_{SG}$; that showed comparable activity (similar TOF values) to Pd/SnBi3$_{SG}$. This proposes that there are different dominant roles other than quantum yield affecting on the photo-oxidation of the former.

EXAMPLE 16

Influence of Catalyst Reuse

Figure 10:
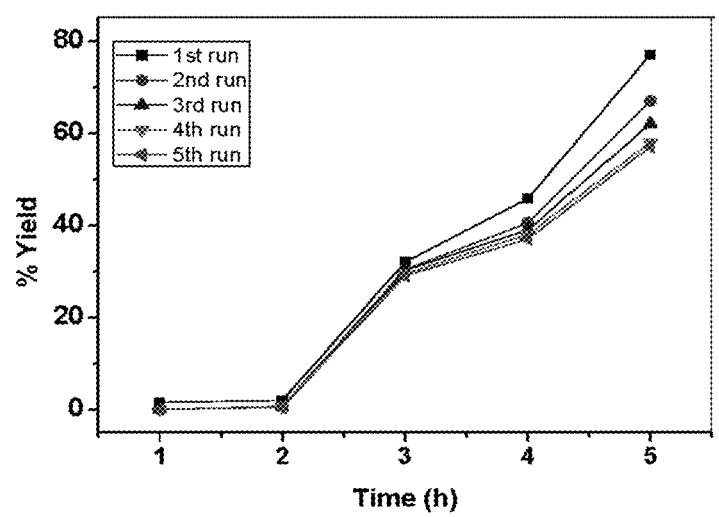
FIG. 10 is a graph illustrating the reusability of $Pd/SnBi3_{SG}$ catalysts for fluorene photo-oxidation. Reaction conditions as in FIG. 6.

One of the economic vital factors in catalytic processes is the stability of the catalyst. In the present work this factor was measured by completing several consecutive experiments with the same catalyst and under uniform operating conditions [FIG. 10]. A direct comparison of the yield obtained when fresh catalyst was used and after five reuses shows that the differences are minimal, indicating that the catalyst has recovered its photo-oxidation activity. A plot of % yield for runs completed with reused catalyst versus time gives an activity comprised of 74% after 25 h. From the previous results, it can be hypothesized that fluorene has been well oxidized on the Pd/SnBi3$_{SG}$ photocatalyst. It has been acknowledged that the adsorption capacity of the previous catalyst remains unchanged, likely the intermediates formed after fluorene oxidation are also oxidized or desorbed into the aqueous bulk as oxidized moieties.

The invention claimed is:

1. A metal oxide supported palladium catalyst comprising a catalyst support comprising a bismuth oxide and a bismuth-tin oxide, and palladium, wherein the palladium is embedded within the catalyst support.

2. The metal oxide supported palladium catalyst as claimed in claim 1, wherein the bismuth oxide comprises $\beta$-$Bi_2O_3$ and the bismuth-tin oxide comprises $Bi_2Sn_2O_7$.

3. The metal oxide supported palladium catalyst as claimed in claim 2, wherein the $\beta$-$Bi_2O_3$ and $Bi_2Sn_2O_7$ are present as a mixture of different crystalline phases and the distance between the $\beta$-$Bi_2O_3$ and $Bi_2Sn_2O_7$ lattice fringes is between 1.3 Å and 1.6 Å.

4. The metal oxide supported palladium catalyst as claimed in claim 1, wherein the atomic ratio of bismuth to tin is 4:1 to 2:1 based on the total number of bismuth and tin atoms in the catalyst support.

5. The metal oxide supported palladium catalyst as claimed in claim 1, comprising 0.1-3.0% palladium by weight based on the total weight of the metal oxide supported palladium catalyst.

6. The metal oxide supported palladium catalyst as claimed in claim 1, wherein the catalyst support is in the form of a crystalline nanoplate-like structure with an average size of 30-60 nm.

7. The metal oxide supported palladium catalyst claimed in claim 1, wherein the catalyst support is in the form of a crystalline nanoplate-like structure with a specific surface area of 5-25 $m^2g^{-1}$, a pore diameter of 2.0-30.0 nm, and a pore volume of 0.10-0.25 $cm^3$/g-Å.

8. A process for producing the metal oxide supported palladium catalyst as claimed in claim 1, comprising
mixing a first solution comprising bismuth ions and a second solution comprising tin ions in the presence of a polyethylene glycol template to form a sol-gel, doping the sol-gel with palladium ions, and reducing the palladium ions.

9. The process for producing the metal oxide supported palladium catalyst as claimed in claim 8, wherein the atomic ratio of bismuth ions to tin ions is 4:1 to 2:1 based on the total number of atoms in the bismuth and tin ion solutions.

10. The process for producing the metal oxide supported palladium catalyst as claimed in claim 8, further comprising
adding an ammonia solution to the bismuth-tin ion solution, heating, autoclaving the formed gel, vacuum drying, and calcining.

11. The process for producing the metal oxide supported palladium catalyst as claimed in claim 8, wherein the source of palladium ions is palladium nitrate.

12. The process for producing the metal oxide supported palladium catalyst as claimed in claim 8, further comprising calcining the catalyst at 300-700° C.

13. A method, comprising
reacting an oxidant and a hydrocarbon under ultraviolet irradiation in the presence of the metal oxide supported palladium catalyst from claim 1.

14. The method, according to claim 13, wherein the hydrocarbon is a polycyclic aromatic hydrocarbon.

15. The method, according to claim 13, wherein the hydrocarbon is fluorene, and the reacting forms a mixture comprising fluorenol/fluorenone oxidation products.

16. The method, according to claim 13, wherein the oxidant is molecular oxygen, and is passed through the reaction mixture for 1-60 minutes at a rate of 1-60 ml/min.

17. The method, according to claim 13, wherein the ultraviolet irradiation source is a high pressure mercury lamp (125 W) with an average light intensity of 50-70 $mWcm^{-2}$ producing ultraviolet light with a wavelength in between 320 and 400 nm.

18. The method, according to claim 13, further comprising
dispersing the metal oxide supported palladium catalyst described in claim 1 and fluorene in a solvent, purging with molecular oxygen, and irradiating.

19. The method, according to claim 13, wherein a catalyst loading is 100-300 mg per 350 ml of fluorene.

20. The method, according to claim 13, further comprising
recovering and reusing the metal oxide supported palladium catalyst in 1-10 reaction iterations.

21. The method, according to claim 13, further comprising
Adding an active species scavenger to attenuate the reactivity of the metal oxide supported palladium catalyst.

* * * * *